(12) United States Patent
Stern et al.

(10) Patent No.: US 9,076,665 B2
(45) Date of Patent: Jul. 7, 2015

(54) CMOS-COMPATIBLE SILICON NANO-WIRE SENSORS WITH BIOCHEMICAL AND CELLULAR INTERFACES

(75) Inventors: Eric D. Stern, Cambridge, MA (US);
Tarek M. Fahmy, New Haven, CT (US);
Mark A. Reed, Monroe, CT (US);
James F. Klemic, Falls Church, VA (US)

(73) Assignee: Yale University, New Haven, CT (US)

( * ) Notice: Subject to any disclaimer, the term of this patent is extended or adjusted under 35 U.S.C. 154(b) by 1480 days.

(21) Appl. No.: 12/517,230

(22) PCT Filed: Dec. 6, 2007

(86) PCT No.: PCT/US2007/024958
§ 371 (c)(1),
(2), (4) Date: Jul. 12, 2010

(87) PCT Pub. No.: WO2008/153552
PCT Pub. Date: Dec. 18, 2008

(65) Prior Publication Data
US 2010/0297608 A1    Nov. 25, 2010

Related U.S. Application Data

(60) Provisional application No. 60/873,740, filed on Dec. 8, 2006, provisional application No. 60/873,070, filed on Dec. 6, 2006.

(51) Int. Cl.
| | |
|---|---|
| *G01N 27/414* | (2006.01) |
| *H01L 29/06* | (2006.01) |
| *B82Y 10/00* | (2011.01) |
| *H01L 29/04* | (2006.01) |
| *H01L 29/16* | (2006.01) |

(52) U.S. Cl.
CPC .............. *H01L 29/0665* (2013.01); *B82Y 10/00* (2013.01); *G01N 27/4146* (2013.01); *H01L 29/045* (2013.01); *H01L 29/0673* (2013.01); *H01L 29/16* (2013.01)

(58) Field of Classification Search
CPC .................................................. G01N 27/4146
See application file for complete search history.

(56) References Cited

U.S. PATENT DOCUMENTS

| | | |
|---|---|---|
| 5,296,719 A | 3/1994 | Hirai et al. |
| 5,972,744 A | 10/1999 | Morimoto et al. |

(Continued)

OTHER PUBLICATIONS

Streifer, et al., "Covalent functionalization and biomolecular recognition properties of DNA-modified silicon nanowires." Nanotechnology vol. 16, Jul. 22, 2005, 1868-1873.

*Primary Examiner* — Melanie Y Brown
(74) *Attorney, Agent, or Firm* — Pabst Patent Group LLP

(57) ABSTRACT

The systems and methods described herein include a sensor for suitable for sensing chemical and biological substances. The sensor comprises a semiconductor layer formed in or on a substrate and a channel having nano-scale dimensions formed in the semiconductor layer, where the structure creates an electrically conducting pathway between a first contact and a second contact on the semiconductor layer. In certain preferred embodiments, the nano-scale channel has a trapezoidal cross-section with an effective width and exposed lateral faces, where the effective width is selected to have same order of magnitude as a Debye length ($L_D$) of the semiconductor material of which the semiconductor layer is formed.

21 Claims, 20 Drawing Sheets

(56) References Cited

U.S. PATENT DOCUMENTS

| | | | |
|---|---|---|---|
| 6,069,380 A | 5/2000 | Chou et al. | |
| 6,870,235 B2 | 3/2005 | Abstreiter et al. | |
| 7,053,439 B2 | 5/2006 | Kan et al. | |
| 2002/0132273 A1 | 9/2002 | Stryer et al. | |
| 2004/0119114 A1* | 6/2004 | King | 257/327 |
| 2004/0121402 A1 | 6/2004 | Harper et al. | |
| 2004/0136866 A1* | 7/2004 | Pontis et al. | 422/57 |
| 2004/0157268 A1 | 8/2004 | Kobilka et al. | |
| 2005/0128788 A1* | 6/2005 | Segal et al. | 365/151 |
| 2005/0255491 A1 | 11/2005 | Lee et al. | |
| 2005/0273867 A1 | 12/2005 | Brulet et al. | |
| 2006/0003333 A1 | 1/2006 | Puskas | |
| 2006/0040378 A1 | 2/2006 | Arinaga et al. | |
| 2007/0048180 A1* | 3/2007 | Gabriel et al. | 422/57 |
| 2007/0096164 A1* | 5/2007 | Peters et al. | 257/253 |
| 2007/0178477 A1* | 8/2007 | Joiner et al. | 435/6 |
| 2007/0196239 A1* | 8/2007 | Vink et al. | 422/82.05 |
| 2007/0231790 A1* | 10/2007 | Su | 435/5 |

* cited by examiner

A

B

C

D

Figure 14
FIGURE 14A
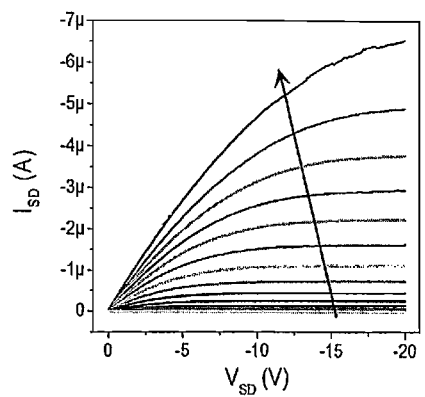
FIGURE 14B
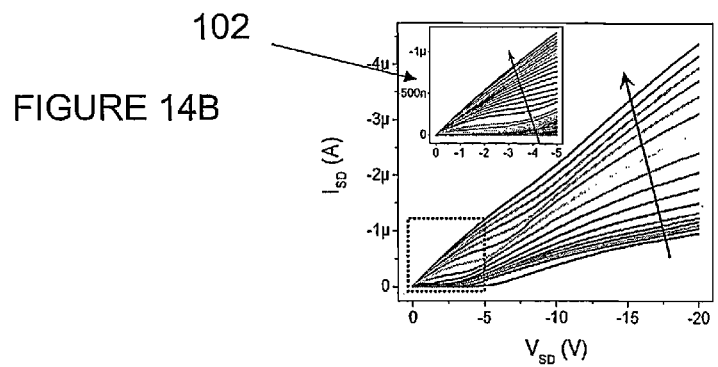
FIGURE 14C
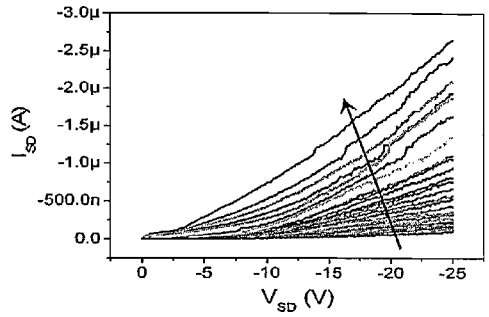

Figure 15
FIGURE 15A
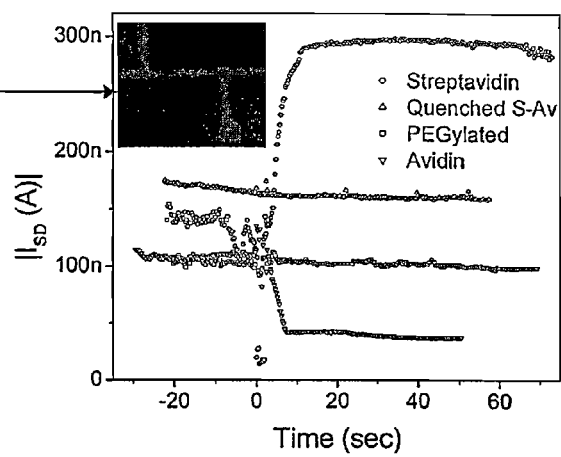
FIGURE 15B
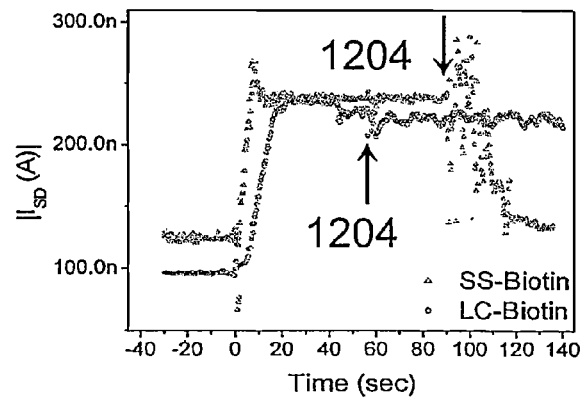

A

B

CMOS-COMPATIBLE SILICON NANO-WIRE SENSORS WITH BIOCHEMICAL AND CELLULAR INTERFACES

CROSS REFERENCE TO RELATED APPLICATIONS

This is a National Stage application of PCT International Application No. PCT/US2007/024958, filed Dec. 6, 2007, which in turn claims the benefit pursuant to 35 U.S.C. §119(e) of U.S. Provisional Application Nos. 60/873,740, filed on Dec. 8, 2006, and 60/873,070, filed on Dec. 6, 2006, each of which is hereby incorporated by reference in its entirety herein.

GOVERNMENT CONTRACT

The U.S. Government has a paid-up license in this invention and the right in limited circumstances to require the patent owner to license others on reasonable terms as provided for by the terms of Contract Nos. ONR K00134, AFOSR L00084, and AFOSR R06868 and graduate student fellowships that are supplied by the Department of Homeland Security and the National Science Foundation.

BACKGROUND OF THE INVENTION

There is an ever-increasing demand for miniature highly sensitive sensor devices suitable for manufacturing and industrial processing applications, environmental monitoring, and as well as defense and homeland security applications. There is also a need for such devices capable of sensitive detection of biochemical and cellular responses in live cells and organisms. Indeed, the ability to rapidly detect minute concentrations of specific macromolecules is especially suited for clinical diagnostics, genomics, and drug discovery. However, conventional macromolecular sensing systems rely on labels, such as radiolabelled tags or fluorophores. There is currently a need in the art for devices, and methods, capable of label-free sensing. These devices, and methods, would likely significantly decrease the time needed for sample preparation, increase sample analysis throughput, and mitigate the need for target molecules modification.

One of the most promising platforms for label-free sensing is nano-wire field effect transistors (NW-FETs). These sensing devices, having the advantage of enhanced sensitivity due to the nano-scale channel confinement, operate by sensing the intrinsic charge of bound molecular species. For example, by binding a receptor protein or a single-stranded DNA (ssDNA) oligomer to the NW-FET surface, the binding of the specific ligand or complementary ssDNA modifies the electric field surrounding the device, enabling direct electronic detection.

Although these, and other, silicon-based nano-sensors have been reported, they have exhibited poor sensing capabilities and their fabrication typically requires complex hybrid manufacturing methods having unreliable product performance and consistency. In addition, typical silicon-based nano-wire fabrication processes exhibit relatively poor material and device service life, thereby further discouraging nano-wire sensor incorporation into larger integrated detector systems.

Hence, there is a need for nano-sensor devices having improved sensing characteristics for enabling accurate and efficient detection of specific reagents in minute concentrations. There is also a need for a simplified fabrication process to produce nano-sensor devices having improved sensing capabilities that may be integrated into a variety of signal processing and information systems.

SUMMARY

The present invention provides nano-sensor semiconductor devices, and methods for their manufacture and use, for detecting chemical/biological substances and monitoring cellular functions where such sensing is based on changes in the device's electrical characteristics, such as electrical conductivity, following exposure to these chemical or biological substances or stimuli for the cellular functions. These nano-sensor devices may incorporate a nano-wire having a large surface to volume ratio that may be fabricated using anisotropic etching such as TMAH (tetramethylammonium hydroxide) or KOH (potassium hydroxide) etching. Such etching is especially preferred since it may produce substantially smooth surfaces and well defined surface edges thereby effecting improved sensitivity.

The nano-sensors of the present invention may include a semiconductor layer formed in or on a substrate. The sensor also includes a nano-wire formed in the semiconductor layer and electrically connected to at least two contacts, where the nano-wire has exposed lateral faces representing the (111) planes of silicon which are natural cleavage planes of crystalline silicon. The substrate of the sensor may be an Si wafer. An electrically insulating layer may be disposed between the substrate and the semiconductor layer. At least two contacts are adapted to form a source and a drain contact, and a gate contact is applied on the side of the nano-wire facing away from the substrate. In an alternative embodiment, the gate contact is electrically connected to the substrate. In other embodiments, one or more gates may lay on top of the semiconductor layer or perpendicular to a direction of current flow in the semiconductor layer. Even though the preferred semiconductor is silicon, other semiconductor materials such as germanium, III-V compound semiconductors and II-VI semiconductors, may also be employed. Semiconductor materials having different crystal orientations may also be employed.

In one embodiment, the semiconductor layer is p-type. In another embodiment, the semiconductor layer is n-type. In yet another embodiment, the semiconductor layer is intrinsic. In certain cases, the nano-wire has a trapezoidal cross-section, where a width at the base of the trapezoid is less than about 200 nm. The height of the nano-wire is less than about 100 nm. In certain cases, the trapezoidal cross-section of the nano-wire has a height that is greater than about 100 nm, but the active region is confined to less than about 100 nm. Although a trapezoidal cross-section is presently preferred, other cross-sectional shapes are also envisioned including, without limitation, square, round, ovoid, or rectangular cross-sections.

In one embodiment, a solution chamber is coupled to the sensor. The solution chamber is adapted to mix a plurality of fluids, where the fluids may be conducive to cellular growth or homeostasis. The solution chamber may be coupled to a nano-sensor to supply the mixed fluids to the sensor for liquid-phase electrical response characterization.

In one embodiment, the nano-sensor may be a free-standing device or an implanted device for sensing various chemical or biological substances as well as cellular functions. The nano-sensor may also be coupled to a variety of microfluidic devices for functioning in a microfluidic system.

In one embodiment, the sensor detects pH or other ionic changes of a substance applied onto its native oxide surface by measuring a difference in conduction current response before and after the application of the substance. The underlying detection mechanism is based on the physical principle of introducing substances that are adapted to interact with the exposed device surface(s) and produce measurable electrical changes as a result of such interaction. In certain implementations, the sensor is a p-type device. In one exemplary application, the sensor is used to monitor real-time cellular responses by sensing activation-induced changes in extracellular pH or other ions that propagate cellular responses.

In one embodiment, a gate structure is coupled to the sensor for tuning sensitivity of the sensor to operate in a desired transconductance range. For example, maximal device sensitivity may be achieved by tuning the sensor to operate at a maximum of the transconductance range. The gate structure may tune the sensitivity of the sensor dynamically via, for example, a feedback loop coupled to the sensor.

Presently preferred methods and devices of the present invention are also capable of selectively detecting minute quantities of particular chemical and biological species by the exposed surface or surfaces of the semiconductor nano-wire to effect label-free species detection. Using these methods and devices, molecules-of-interest need not be specially conditioned to be detected and such detection may be performed in the presence, or absence, of a functionalized device surface. Nano-wire field effect transistors (NW-FETs), for example, can serve as ultrasensitive detectors for label-free reagents. These nano-sensor devices exhibit improved surface charge sensitivity due to their large surface area-to-volume ratio. Without being limited by theory, NW-FET sensing may be affected by the local channel electric field created by the binding of charged molecules to the nano-wire surface. Additional surface charges strongly influence the size of the NW-FET depletion layer, thereby modulating channel current. Thus, when configured as solution-phase sensors, these devices are ideal for monitoring pH changes such as those induced by cellular metabolic activity. Still further, Debye length modification may facilitate improved detection of macromolecules, by selective binding of macromolecules species, using NW-FET sensors.

In one embodiment, the sensor is adapted to detect a binding of a macromolecule to a receptor molecule that is functionalized onto a surface of the sensor. This detection is accomplished based on the sensor sensing a difference in conduction current response before and after the binding. In certain implementations, dec-9-enyl carbamic acid tert-butyl ester may be used to functionalize the surface of the sensor. In certain implementations, the nano-sensor is functionalized with macromolecules such as nucleotides, proteins, carbohydrates or mixtures that stimulate specific responses in certain cells. In particular, the cellular responses may be detected by a measured change in conduction current due to the interaction of the macromolecules with the cells.

In one embodiment, the sensor is incorporated into an integrated CMOS system to perform at least one of signal processing, error detection, and complementary error detection, where the integrated CMOS system includes at least one of an n-type sensor device and a p-type sensor device for conducting complementary sensing.

According to another aspect of the invention, a method for producing a nano-wire sensor is provided. The method includes providing a substrate with an electrically conducting semiconductor layer disposed on the substrate and electrically isolated from the substrate. Then a masking layer overlaying a portion of the semiconductor layer is formed, where the masking layer includes an area for forming a nano-wire on the substrate. Subsequently, the semiconductor layer is removed around the masking layer and the semiconductor layer is laterally etched underneath the masking layer to expose the (111) planes of the semiconductor layer. The etching is terminated when lateral dimensions of the resulting nano-wire are less than about 200 nm. In one implementation, the lateral etching includes applying a TMAH etch.

Further features and advantages of the present invention will be apparent from the following description of exemplary embodiments and from the claims.

BRIEF DESCRIPTION OF THE DRAWINGS

These and other features and advantages will be more fully understood by the following illustrative description with reference to the appended drawings, in which like elements are labeled with like reference designations, and in which the drawings may not be drawn to scale.

FIGS. 14A and 14B illustrate source-drain current ($I_{SD}$) versus source-drain voltage ($V_{SD}$) for various gate-drain voltages (VGD) applied to an unfunctionalized p-type nano-wire sensor and a p-type nano-wire sensor functionalized with dec-9-enyl carbamic acid tert-butyl ester.

FIG. 14C illustrates $I_{SD}$, versus $V_{SD}$ for various VGD applied to a p-type nano-wire sensor functionalized with 1-decene.

FIG. 15A illustrates conduction current responses in biotin-functionalized p-type nano-wire sensors to the addition of streptavidin, quenched streptavidin, and avidin. Current response is also shown for a poly(ethylene glycol) (PEG) functionalized sensor device to the addition of streptavidin.

FIG. 15B demonstrates the reversibility of p-type nano-wire sensor response to streptavidin addition and removal.

DETAILED DESCRIPTION OF THE INVENTION

Certain preferred embodiments of the present invention provide devices, and methods for their production, especially suited to sense a variety of molecular species, biological species, or cellular responses. In this manner, the species and/or substances of-interest may be detected and/or monitored. These species or substances can be present in solid, liquid or gaseous state in the ambient or can be applied to the device. Sensors of the present invention, for example, are especially suited for detecting, measuring, or both, of proteins, DNA and intrinsic cellular changes or cellular changes due to extrinsic stimuli. Still further, sensors, as described and provided herein, may also be suitable for sensing cellular interactions due to paracrine, autocrine, or endocrine signaling, or combinations thereof. The detection device is implemented as an elongated nanostructure, for example, a nano-wire, and has an exposed surface that is substantially smooth and well defined. The nanostructure may be fabricated on a semiconductor substrate or on a semiconductor-on-insulator (SOI) substrate, wherein TMAH wet-etching is preferred. The exposed surface of the device used for detection may or may not be functionalized depending on the device's applications.

Figure 1:
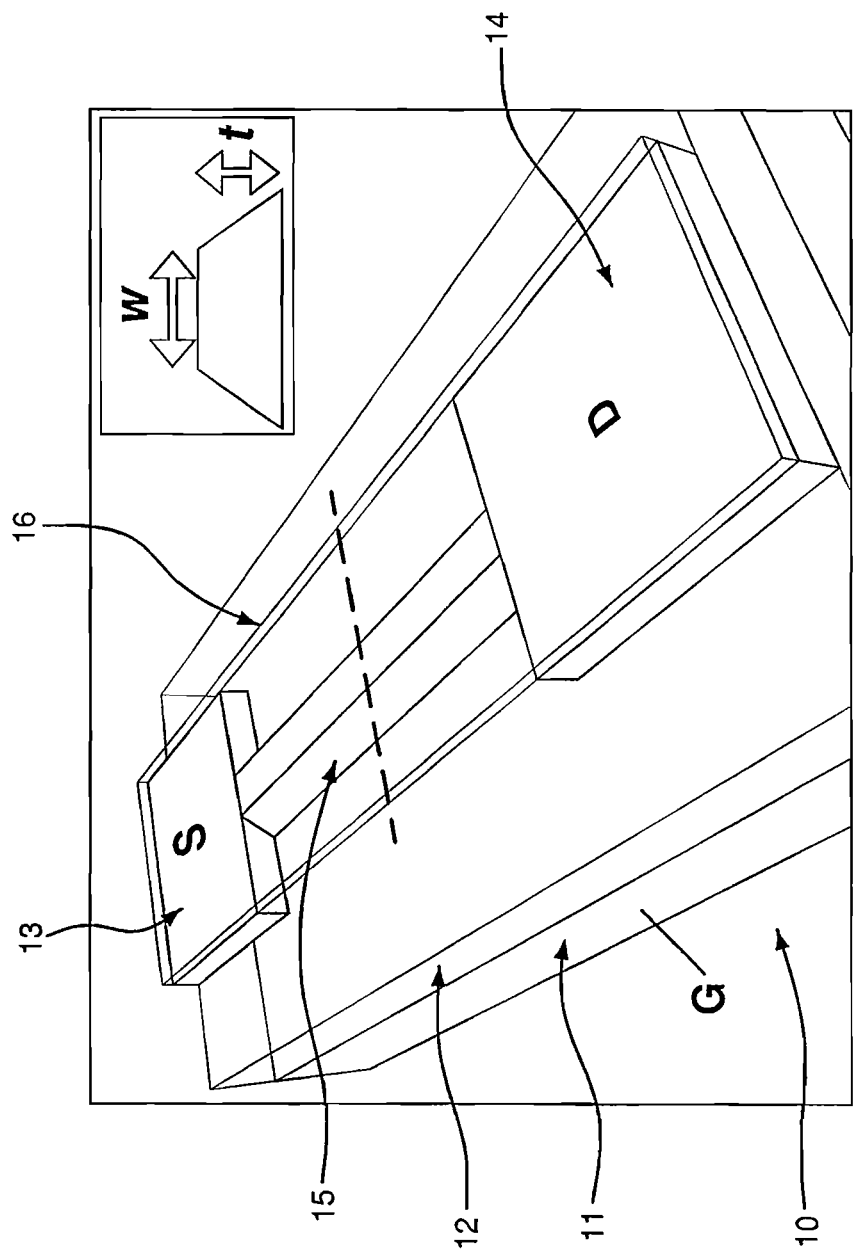
FIG. 1 shows a schematic diagram of a nano-wire device, according to one embodiment of the invention, after anisotropic etching and before removal of the 600 nm wide masking oxide.

FIG. 1 shows a schematic diagram of a nanostructure sensor according to one embodiment of the invention. In this embodiment, the device is fabricated on a (100) silicon-on-insulator (SOI) wafer 10 which includes a silicon substrate 11, a thin $SiO_2$ layer 12 on the Si substrate 11 and a top Si layer on the $SiO_2$ layer 12, in which the source (S) contact 13, the drain (D) contact 14 and the actual nanostructure device 15, subsequently also referred to as nano-wire 15, are defined. Also shown is a $SiO_2$ layer 16 overlaying the contact 13, 14 and the device 15. The $SiO_2$ layer 16 in the illustrated example has a width of about 600 nm, from which the nano-wire device with a final width w (see inset) is then etched. The term "nano-wire" is not meant to imply that all lateral surfaces of the nano-wire are accessible from the outside. In the illustrated embodiment, the nano-wire 15 is prepared from the top Si layer and the bottom surface of the nano-wire 15 is therefore in direct material contact with the $SiO_2$ layer 12 and thus inaccessible.

The inset in FIG. 1 shows a cross-sectional view of the nano-wire 15 with a trapezoidal shape of thickness t and width w defined by the processing steps, which will be described in detail below. The sloped surfaces of the trapezoid represent the natural Si (111) planes, or cleavage planes, and may have an angle of about 54.7° between the (100) plane and the (111) plane.

Figure 2:
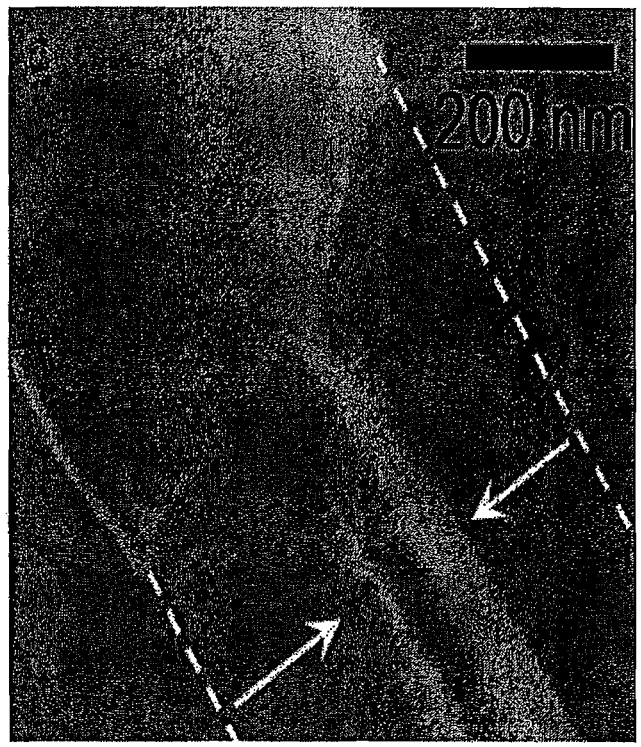
FIG. 2 shows a scanning electron micrograph (SEM) of a completed device illustrating the x≈200 nm undercut etched from the sides of the masking oxide. The final device is 80 nm wide.

FIG. 2 shows a scanning electron micrograph (SEM) of a detail near the source contact 13 of a finished device, where the top $SiO_2$ layer 16 has been removed. Although pattern-defined roughness is discernible near the contact regions, the sides of the device (i.e., the etched (111) silicon planes) appear substantially smooth without any visible surface roughness. Nano-wires with a controlled width of between about 50 nm and about 200 nm have been successfully prepared.

The width of the devices may be selected to optimize device sensitivity. As those skilled in the art will appreciate, the exemplary nano-wires form a conductive pathway between the contact regions 13 and 14 which, in the sensing operation, is affected by surface charges formed or deposited on or near the exposed lateral surfaces. These surface charges induce the greatest changes in the conductive pathway if they affect a substantial portion of the trapezoidal cross section of the device. The depth by which the surface charges extend from the exposed lateral surfaces inward is governed by the depletion width that in turn depends on the Debye length ($L_D$) of the semiconductor material from which the nano-wire is formed. The semiconductor characteristic Debye length may be presented as:

$$L_D \equiv \sqrt{\frac{\varepsilon_s kT}{q^2 N_B}} \quad (1)$$

wherein q is the electron or hole charge, $N_B$ is the doping density, T is the absolute temperature, and $\varepsilon_s$ is the dielectric constant of the semiconductor material. Exemplary values for $L_D$ at room temperature are $L_D \approx 100$ nm for $N_B=10^{15}$ cm$^{-3}$, and $L_D \approx 10$ nm for $N_B=10^{17}$ cm$^{-3}$. The values for $L_D$ of GaAs are identical to those of Si, whereas the values for Ge are greater by a factor of 1.16 due to the larger dielectric constant. The depletion width of the conduction nano-wire pathway, which depends on the Debye length ($L_D$) of the semiconductor material, can be changed by applying a gate voltage to a gate contact. The gate contact may be the silicon layer 11, operating as a back gate, or another contact layer disposed above the nano-wire 15, operating as a top gate (not shown).

In further detail, the charge of solution-based molecules and macromolecules is screened by dissolved solution counterions: a negative species such as streptavidin or DNA will be surrounded by positively charged ions due to electrostatic interactions. Accordingly, molecular charge screening by dissolved solution counterions—Debye screening—on sensor response can be evaluated. At a characteristic Debye length ($\lambda_D$), the number of net positive charges approaches the number of negative charges on the protein or DNA. The result is a screening effect such that the electrostatic potential arising from charges on the protein or DNA decays exponentially toward zero with distance. For aqueous solutions at room temperature, this Deybe length ($\lambda_D$) may be re-written from its previously described equation and now presented as:

$$\lambda_D = \frac{1}{\sqrt{4\pi d_B \sum_i \rho_i z_i^2}}, \quad (2)$$

where $l_B$ is the Bjerrum length=0.7 nm, $\Sigma_i$ is the sum over all ion species, and $\rho_i$ and $z_i$ are the density and valence, respectively, of ion species i. Thus, for optimized sensing, the Debye length must be carefully selected for NW-FET measurements since molecules binding to the devices are likely removed from the sensor surface by approximately 2-12 nm (the size of the receptor proteins or DNA linkers bound to the sensor surface). Debye length considerations, such as those now discussed, should likely be considered when designing preferred optimized protocols for label-free sensing, and such considerations may facilitate improved label-free sensing using NW-FETs. Indeed, proper consideration and optimization of Debye length selection ($\lambda_D$) may facilitate selective label-free sensing of macromolecules.

Figure 3:
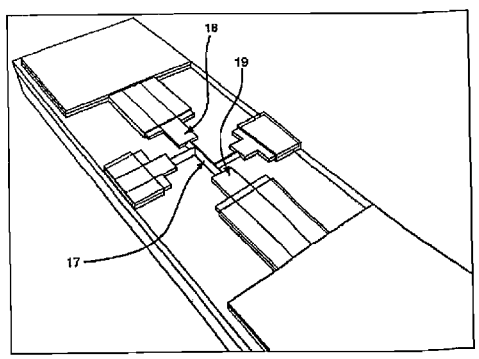
FIG. 3A shows a schematic diagram (not to scale) of a four-point NW-FET device with source S, drain D, and gate G defined for a two-point sensing configuration. The TMAH-etched active sensing region 17 is shown.
FIG. 3B shows a scanning electron micrograph of a 4-point NW-FET device having a in-line lead length of 30 μm.
FIG. 3C shows $I_{SD}$ ($V_{SD}$) dependence for $V_{GD}$ varied in −2V steps for a representative device in air before APTS functionalization.
FIG. 3D shows $I_{SD}$ ($V_{SD}$) dependence for $V_{GD}$ varied in −2V steps for a representative device in air after functionalization with APTS.
Figure 3:
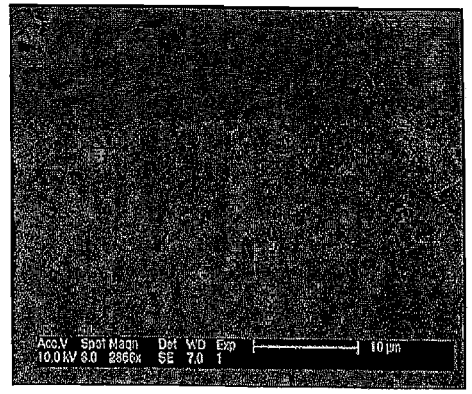
Figure 3:
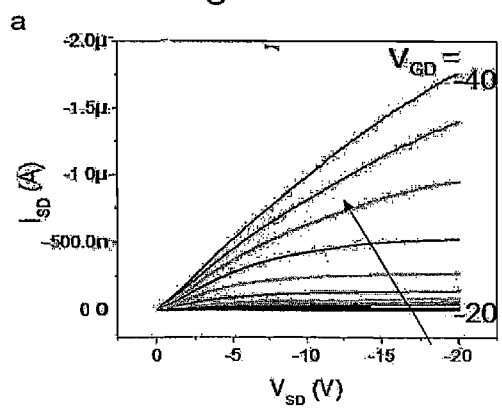
Figure 3:
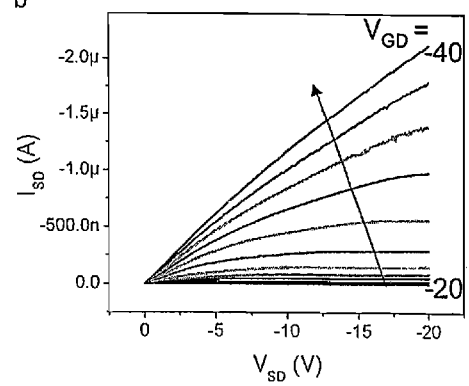

In one preferred aspect of the present invention, nanowire-FET devices may be fabricated from silicon-on-insulator (SOI) wafers. For example, the NW-FET device regions may be defined with a wet chemical etch (tetramethylammonium hydroxide, TMAH), which etches Si (111) planes at approximately 1/100 the rate of all other planes and thereby eliminates edge imperfections not aligned to this plane. Electron-beam lithography and subsequent reactive-ion etching may be used to define the device dimensions in a thermally grown masking oxide, and TMAH etching to subsequently transfer the pattern to the active silicon layer. It should be noted that this etch produces trapezoidal devices due to the (100) orientation of the SOI wafers. As illustrated in the schematic in FIG. 3A, the etching causes undercutting of the masking oxide into the lightly-doped region (boron, $10^{15}$ cm$^{-3}$) 17, which in turn facilitates devices with significantly smaller dimensions than originally defined. The doped source contact 18 and drain contact 19 (each doped to $>10^{20}$ cm$^{-3}$ with boron by ion implantation) extend under the metal contact pads and are not appreciably etched by the TMAH. A scanning electron micrograph of a such an NW-FET device is shown in FIG. 3B. Four-point measurements showed that such devices exhibit negligible contact resistance such that sensing measurements can be made in a two-point configuration, as depicted in FIG. 3A.

The transport characteristics of such device were measured before and after surface functionalization since surface chemistry interactions have been shown to have a deleterious effect on sensing properties. The dependence of source-drain current ($I_{SD}$) on source-drain voltage (V$_{SD}$) for varying gate-drain voltage (V$_{GD}$) for a representative device is shown in FIG. 3C. In the instant case, sensing measurements used direct current having V$_{SD}$=-2V and V$_{GD}$=-35V. The large V$_{GD}$ required to turn on the device is consistent with SOI accumulation-mode operation. FIG. 3D shows that device functionalization with 3-aminopropyltriethoxysilane (APTS) to convert silanol (Si—OH) groups to free amines did not significantly affect the $I_{SD}$ (V$_{SD}$) of the device. The relatively minute increase in $I_{SD}$ for large V$_{GD}$ suggests the presence of a small parallel current path through the surface. However, this path was not shown to appreciably alter the electronic characteristics when the device is fully depleted (V$_{GD}$≥-20V).

As mentioned above, the device structure, including the nano-wire 15, the contact regions 13, 14 and the contact to silicon layer 11, which may operate as a back gate, are fabricated on 4" diameter SOI wafers 10. The active Si layers were thinned to about 25 nm, about 40 nm, and about 80 nm by oxidation followed by wet etching.

Figure 4:
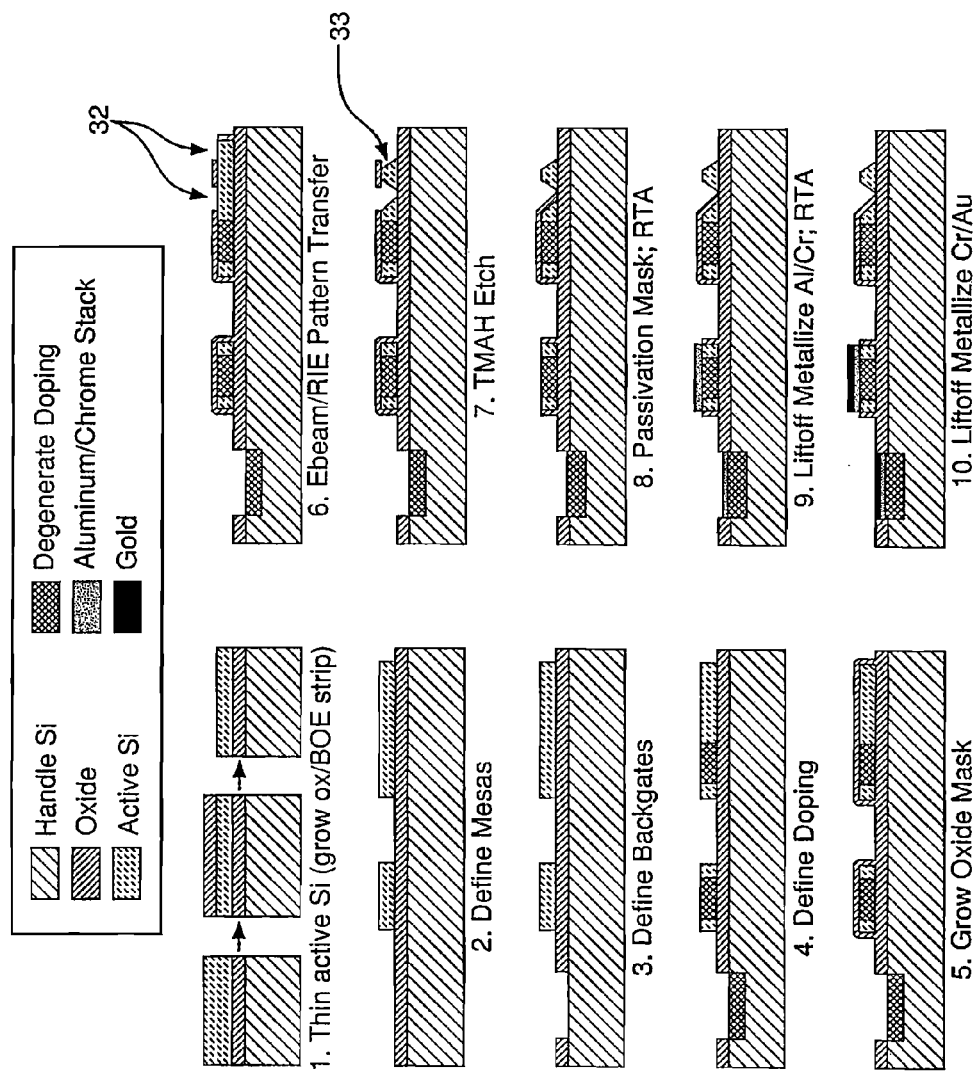
FIG. 4 shows the processing steps for fabricating the nano-wire sensor device according to the invention.

An exemplary process for fabrication of the nano-wires according to one embodiment of the invention is depicted in FIG. 4. Step 1 shows the formation of an oxide by thermal oxidation of the top (active) Si layer of the wafer; the thermal oxide is then removed in a buffered oxide etch (BOE), leaving an active Si layer with a reduced thickness. In Step 2, those areas on the wafer 10 which will later define the source and drain contacts 13, 14 (as referenced by FIG. 1) and the region where the actual nano-wire 15 is formed, are delineated by contact lithography, and the top silicon layer outside the delineated areas is etched off by RIE to form mesas. Because the nano-wire is formed in a later process step (Step 7) by exposing the Si (111) surfaces, the silicon wafer is aligned at this point with the <110> wafer flat perpendicular to the orientation of the nano-wire. In Step 3, optical lithography and a two-step RIE are used to define a contact area for access to the back gate 11 (FIG. 1) and alignment marks in the handle wafer. In Step 4, the degenerate contact areas for the source contact 13 and the drain contact 14 are defined by optical lithography and formed by ion implantation. Arsenic ions are implanted for n-type conducting nano-wires (inversion-mode devices), and boron ions are implanted for p-type conducting nano-wires (accumulation-mode devices).

In Step 5, a thermal masking oxide (see layer 16 in FIG. 1) is grown over the implanted mesas and the gate contact area. In Step 6, the nano-wire pattern is transferred to the masking oxide by e-beam lithography and the masking oxide is removed in the unexposed areas, as indicated by the arrows 32. The areas outside the pattern shown in FIG. 1 with the reference symbol 16 are then etched down to the SiO$_2$ layer 12 by RIE, leaving the mesa defined by the area under the masking oxide 16 (see FIG. 1).

In Step 7, the wafer is etched in an anisotropic wet etch, in the present embodiment tetramethyl ammonium hydroxide (TMAH), which etches the Si (111) planes about 100 more slowly than other Si planes. Etching in TMAH retains the pattern defined by the masking oxide layer, but smoothes edge imperfections not aligned with the Si (111) plane.

Figure 5:
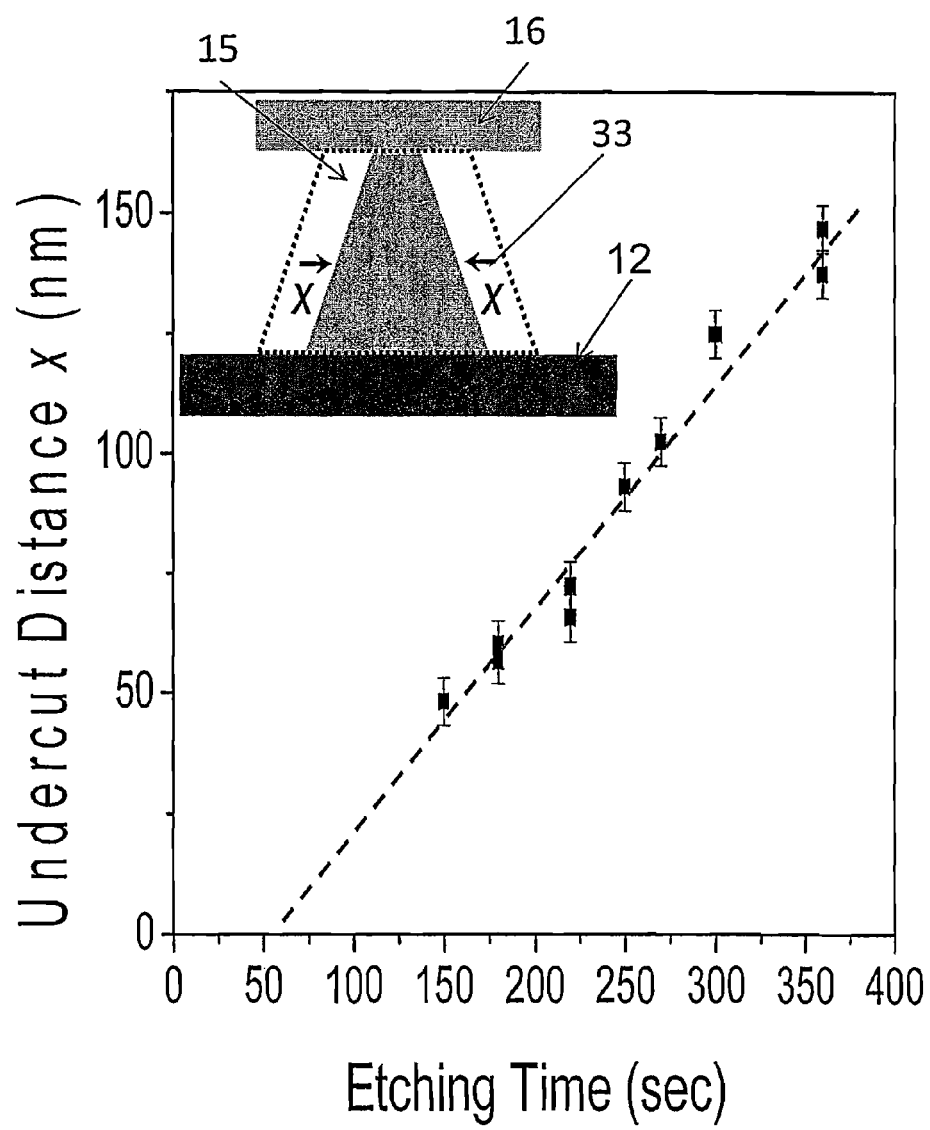
FIG. 5 demonstrates control of the lateral undercut distance as a function of the etching time for a TMAH etch.

FIG. 5 demonstrates the feature size control achieved with the TMAH etch. Plotted is the undercut distance x (in nm) as a function of the etch time (in sec). The thickness of the active Si layer was t=80 nm and four devices are investigated. At each etch time, an average laterally TMAH-etched distance x is shown for four devices, with the error bars representing one standard deviation, indicating a feature size control of better than about 10 nm.

Returning now to FIG. 4, in Step 8, optical lithography and BOE are used to remove the masking oxide from the contact pads and the active nano-wire device, leaving the nano-wire exposed, as shown in FIG. 2. The samples are then annealed in forming gas in a Rapid Thermal Annealing (RTA) step. In Step 9, the contact area is delineated by optical lithography and metal contact pads are deposited on the source and drain contact pads 13, 14 and the gate contact area. The metal contacts pads are fabricated by conventional lift-off Aluminum (99.999%, Kurt J. Lesker Co.)/Chromium (99.998%, Kurt J. Lesker Co.) metallization followed in Step 10 by optical lithography and a Chromium/Gold metal stack deposited by lift-off. Those skilled in the art will appreciate that other metals compatible with silicon processing technology, in particular CMOS processing, may be employed.

The afore-described fabrication process is flexible, allowing the configuration of a variety of sophisticated nano-wire geometries; for example, a 6-terminal Hall sensor, a 4-terminal device for accurate resistance characterization, and the described 2-terminal sensor. Sensor arrays and integrated signal processing electronics may be readily fabricated as well.

Figure 6A:
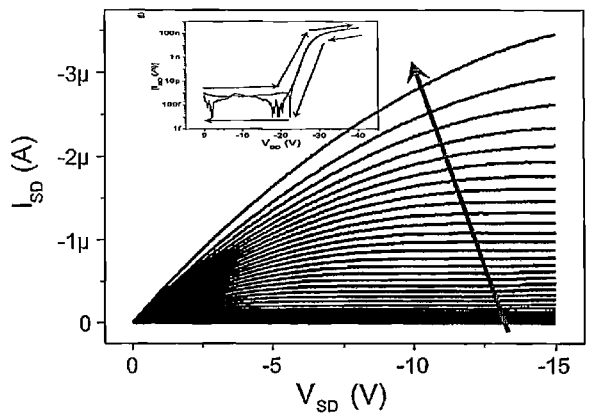
FIG. 6A shows the electrical device characteristics of a p-type sensor.

FIG. 6A shows the source-drain current (I$_{SD}$) as a function of the source-drain voltage (V$_{SD}$) of a p-type device (boron-doped silicon active layer) for various gate-drain voltages (V$_{GD}$) between 0 V to –40V in –1V steps (indicated by the bold arrow). The device has a width w≈50 nm, a thickness t≈25 nm and a length of 20 μm. The characteristics show p-type accumulation mode behavior. The inset in FIG. 6A shows for the same p-type devices the source-drain current (I$_{SD}$) as a function of the gate-drain voltage (V$_{GD}$) for constant source-drain voltage (V$_{SD}$) of =–1V for a forward and reverse sweep, indicated by the arrows. The slope of this curve is commonly referred to as transconductance (g$_m$). The device hysteresis is seen to be minimal.

Figure 6B:
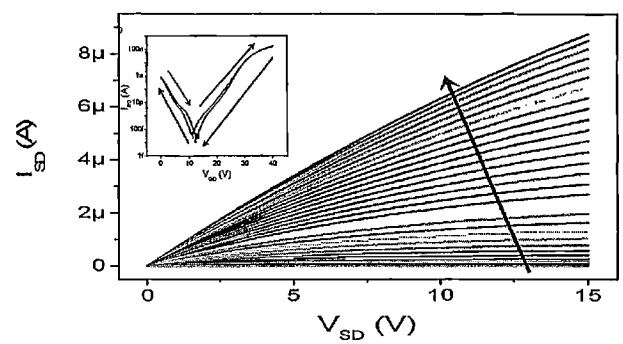
FIG. 6B shows the electrical device characteristics of an n-type sensor.

FIG. 6B shows the corresponding curves for n-type devices (arsenic-doped silicon active layer). The device has a width w≈50 nm, a thickness t≈40 nm and a length of 20 μm. The gate-drain voltage (V$_{GD}$) is varied between 0 V and +40V in steps of –+1V (indicated by the bold arrow). The characteristics show n-type inversion mode behavior. The almost imperceptible hysteresis between forward and reverse I$_{SD}$ (V$_{GD}$) in the region of maximum transconductance (steepest slope; see inset) suggest minimal defect-induced charge trapping.

Figure 6C:
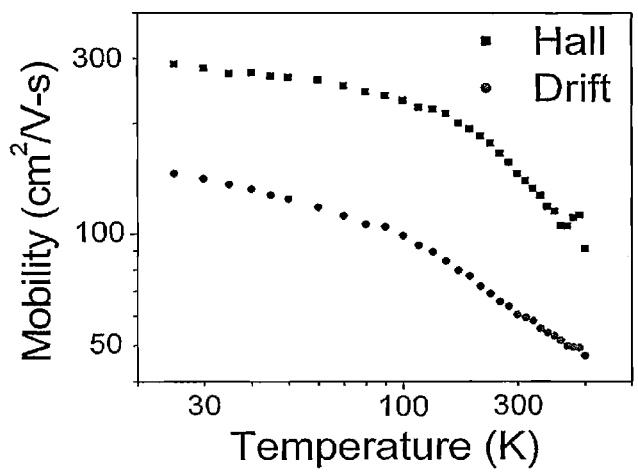
FIG. 6C shows the drift and Hall mobilities for a p-type test structure.

In one embodiment, the Hall bar configuration of a silicon nano-wire makes it possible for the first time to measure the Hall mobility in the nano-wire, as shown in FIG. 6C. The peak drift mobilities may be calculated from the measured I$_{SD}$ (V$_{GD}$) dependence and a self-consistent device simulation (Silvaco®). As depicted in FIG. 6C, an approximate average drift mobility of about 54 cm$^2$/Vs is obtained, with a maximum value of 139 cm$^2$/Vs. The device had a width w≈300 nm, and a thickness t≈25 nm. These results compare favorably with mobility data for bulk p-type silicon doped to 10$^{15}$ cm$^{-3}$, which has a bulk mobility of 450 cm$^2$/Vs. Hole mobilities are typically smaller than electron mobilities by about a factor of 2. The bulk mobility is known to decrease for anisotropically defined Si (111) planes.

This described device fabrication process provides inherent back-gating capability of the nano-wire channel, which permits the sensitivity of a device to be tuned through operation in different transconductance (g$_m$) regions, which is important for applications requiring a high dynamic range. Transconductance is a measure of the dependence of the source-drain current I$_{SD}$, on the gate voltage V$_{GD}$ and may be presented as:

$$g_m = \left(\frac{\partial I_{SD}}{\partial V_{GD}}\right)_{V_{SD}=const} \quad (3)$$

The sensor response to changes in the surface charge will occur at the maximum transconductance value (g$_{m,max}$). This maximum value is reached between the linear region and the saturation region of an FET transfer characteristic.

The useful gate voltage V$_{GD}$ for optimized device performance depends on the actual device parameters, for example, the electric field induced by the gate in the conductive channel of the nano-wire, i.e., the thickness of the SiO$_2$ layer 12 (FIG. 1). In the described exemplary embodiments, this SiO$_2$ layer 12 is quite thick, typically about 100 nm, so that large gate voltages V$_{GD}$ are required. A decrease of the gate voltage can be expected with a thinner SiO$_2$ layer 12.

As mentioned above, both boron-doped p-type devices and arsenic-doped n-type devices can be prepared. Fabrication of these complementary devices is compatible with conventional silicon CMOS processing. The nano-wire sensor devices can therefore become part of an integrated system with on-chip signal processing, error detection, and complementary detection to avoid false positives. Complementary devices are useful for detecting, for example, small concentrations of antibodies, which will be described in detail below.

The active region of the nano-wire devices may be between about 1 μm to about 100 μm long, with a thickness between about 25 nm to about 100 nm. A width at the top of the trapezoidal cross-section may be etched down to about 10 nm. In general, the thinner the active region of the nano-wire, the larger its surface area-to-volume ratio.

Although the illustrated nano-wire devices in the exemplary embodiments are fabricated on an SOI wafer with the underlying silicon substrate operating as a back gate, a gate electrode can also be applied on top of the nano-wire. Alternatively, the top silicon active layer can be insulated from the substrate by a reverse biased p-n junction. In an alternative embodiment, the nano-wires may be formed in compound semiconductors, such as GaAs, GaAlAs, GaAlInAsP and other III-V compound semiconductors, or in any other materials that exhibit a low intrinsic surface state density that can be altered by an externally applied surface charge. As compound semiconductor layers with different composition respond differently to chemical etchants, the fabrication of devices in compound semiconductor materials may include the formation of etch stop layers which may be used to define the narrow dimensions of nano-wires.

Figure 7:
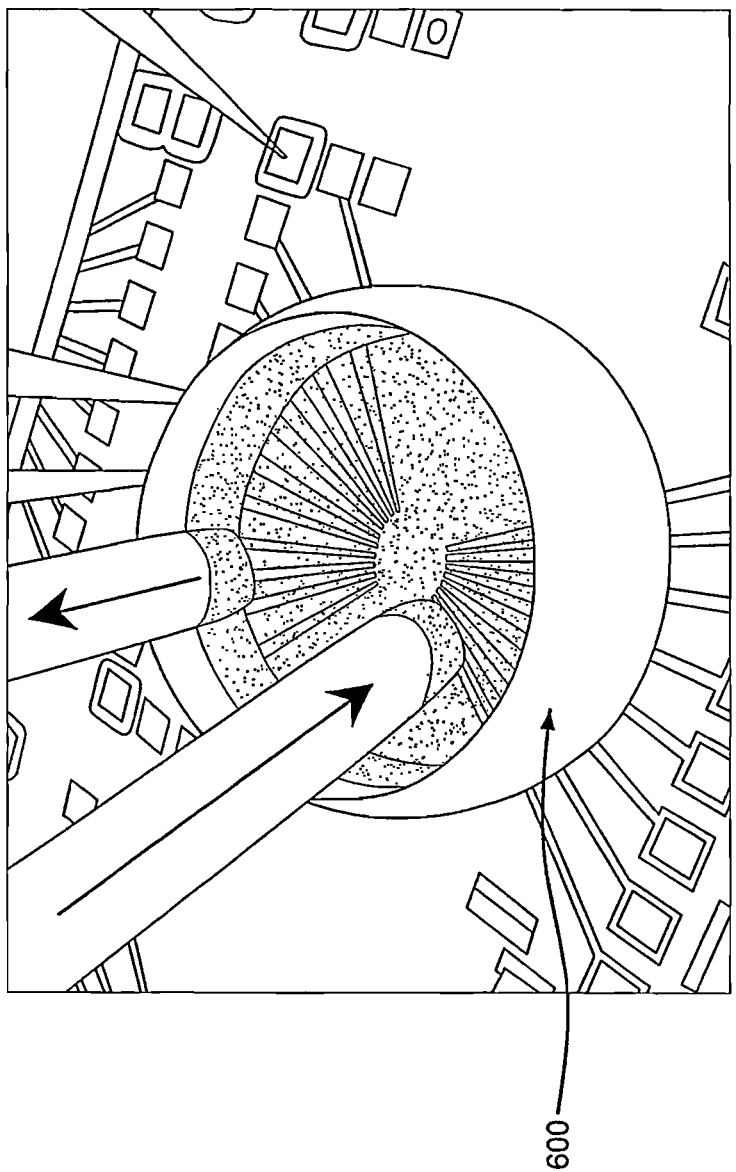
FIG. 7 illustrates a solution chamber according to one embodiment of the invention.

In certain embodiments, a macro-scale solution chamber 600 is provided to facilitate the characterization of liquid-phase sensor response by the nano-wire device. FIG. 7 illustrates an exemplary solution chamber 600 configured to induce mixing of fluids that are continuously supplied to the nano-wire structure for solution-based electrical response measurement. These fluids may be specific media that are conducive to cellular growth or homeostasis. In a preferred configuration, this solution chamber 600 is designed to avoid the well-characterized limits on sensitivity and response time inherent in diffusion-limited systems, such as in microchannels.

According to one aspect of the invention, the nano-wire structure of FIG. 1 acts as a sensor for monitoring ionic changes of various substances. More specifically, substances of varying ion compositions, when introduced onto the native oxide surface of the nano-wire device, are adapted to alter the nano-wire's surface potential and effectively gating the underlying device. Hence, the nano-wire structure provides a sensitive and measurable means by which ionic changes of various substances may be accurately monitored in real-time. For example, given a p-type nano-wire device, if the pH of a solution introduced to the surface of the nano-sensor is lower than pH of the device's native oxide coating, then the absorption of the solution onto the oxide coating results in the protonation of the oxide surface, thus depleting the hole-carriers in the device, resulting in an increase in its surface charge density, and causing a decrease in its source-drain conductivity. Conversely, when a solution having a higher pH level is introduced to the p-type nano-sensor, the sensor's oxide surface is adapted to deprotonate, causing a subsequent decrease in its surface charge density and an increase in its conductivity. In addition, n-type nano-wires are equally operable as miniaturized sensors for the screening of real-time molecular responses. N-type nano-wire structures will be described below in greater detail. In certain implementations, the unfunctionalized nano-sensors show enhanced device sensitivity towards interaction-dependent conductivity responses when the device surface area is reduced. In certain implementations, the nano-sensors display favorable characteristics such as small hystereses and high reproducibility, where the average detected current levels are repeatable to less than about 15% error.

Figure 8:
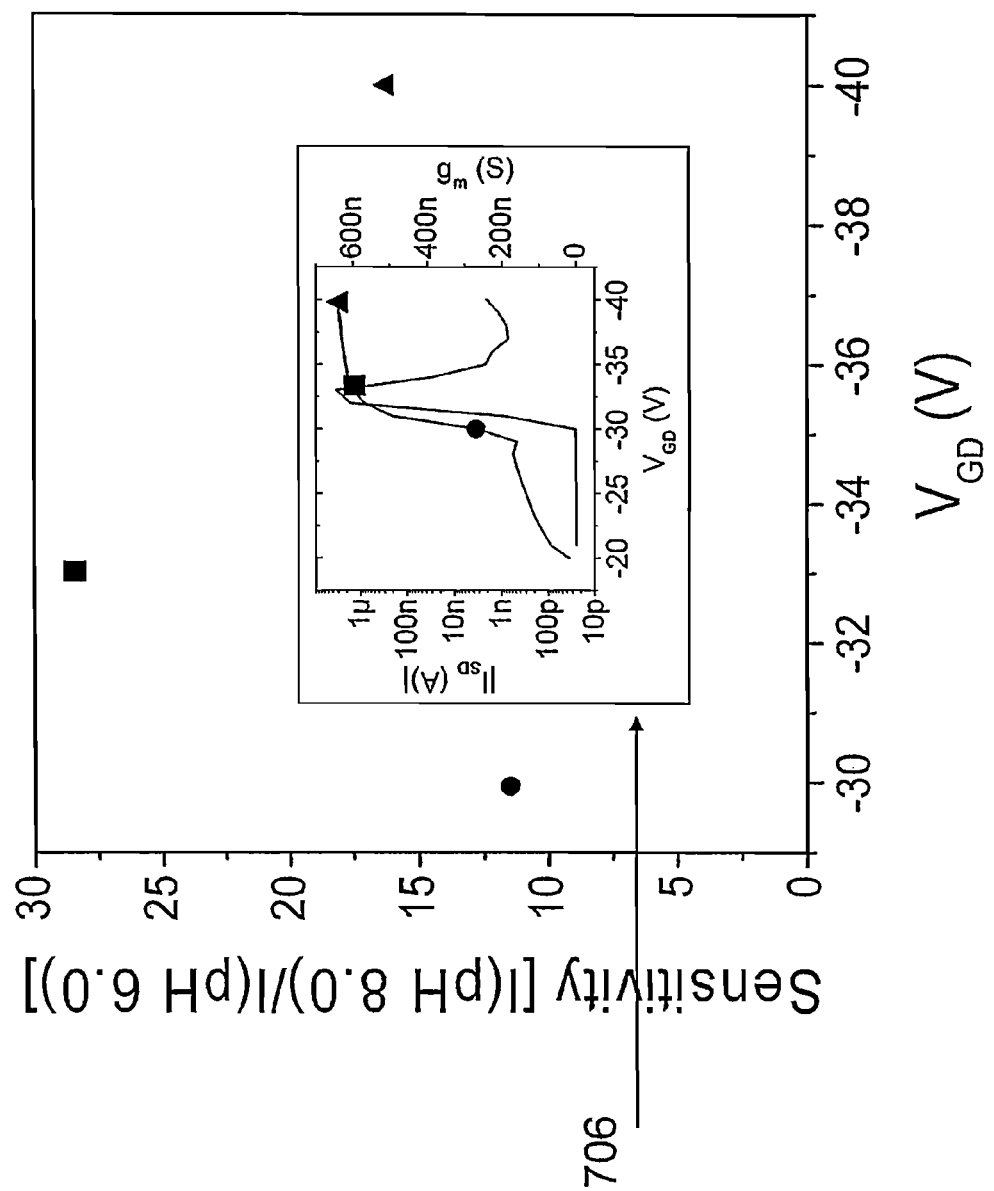
FIG. 8 illustrates sensitivity and transconductance responses, both as functions of gate-drain voltage, in an unfunctionalized p-type nano-wire sensor.

In one embodiment, the unfunctionalized nano-sensors of the present invention is implemented into an architecture containing a back-gate for tuning the sensitivity of the device to operate within a specific transconductance ($g_m$) region. In general, transconductance is a measure of current response with respect to gate voltage. Thus, transconductance measurements provide a quantifiable approach for a user to tune the sensitivity of the nano-sensor to sense specific substances whose detection is desirable to the user. Inset 706 of FIG. 8 provides an exemplary plot of a sensor's source-drain current $I_{SD}$ and transconductance $g_m$ dependencies on gate-drain voltage $V_{GD}$ at a constant source-drain voltage $V_{SD}$ of −1 V. With reference to FIG. 1, the sensor has a cross-sectional thickness of about 40 nm and a cross-sectional width of about 150 nm, where this cross-sectional width refers to the smaller of the trapezoidal widths characterizing the device's cross section. FIG. 8 also illustrates a plot of the sensor's sensitivity ratio as a function of $V_{GD}$. As depicted, the sensor's measured sensitivity tracks with its measured transconductance over the range of $V_{GD}$ values. In particular, FIG. 8 shows that the most sensitive sensor response to additional surface charge occurs at the maximum transconductance state $g_{m,max}$, which is between the linear and saturation regions of the device's transfer characteristic. Hence, the sensitivity of a nano-sensor may be optimized by applying appropriate voltages to the back-gate such that the sensor device is operating at $g_{m,max}$. Due to the dynamic range of sensitivities provided by gating, a nano-sensor may also be tuned to a sensitivity level as specified by a user. For example, the back-gate is used to tune chemical potential of the nano-sensor to a particular reaction such that only the signal from that reaction is electronically recognized by the sensor. Furthermore, a dynamic feedback loop may be coupled to the tunable nano-sensor device to perform automatic and optimized sensitivity correction. In addition, one or more top-gates, lateral-gates, side-gates or any combination thereof are used to tune the nano-sensor to operate within a specific transconductance, and hence sensitivity, state.

Figure 9:
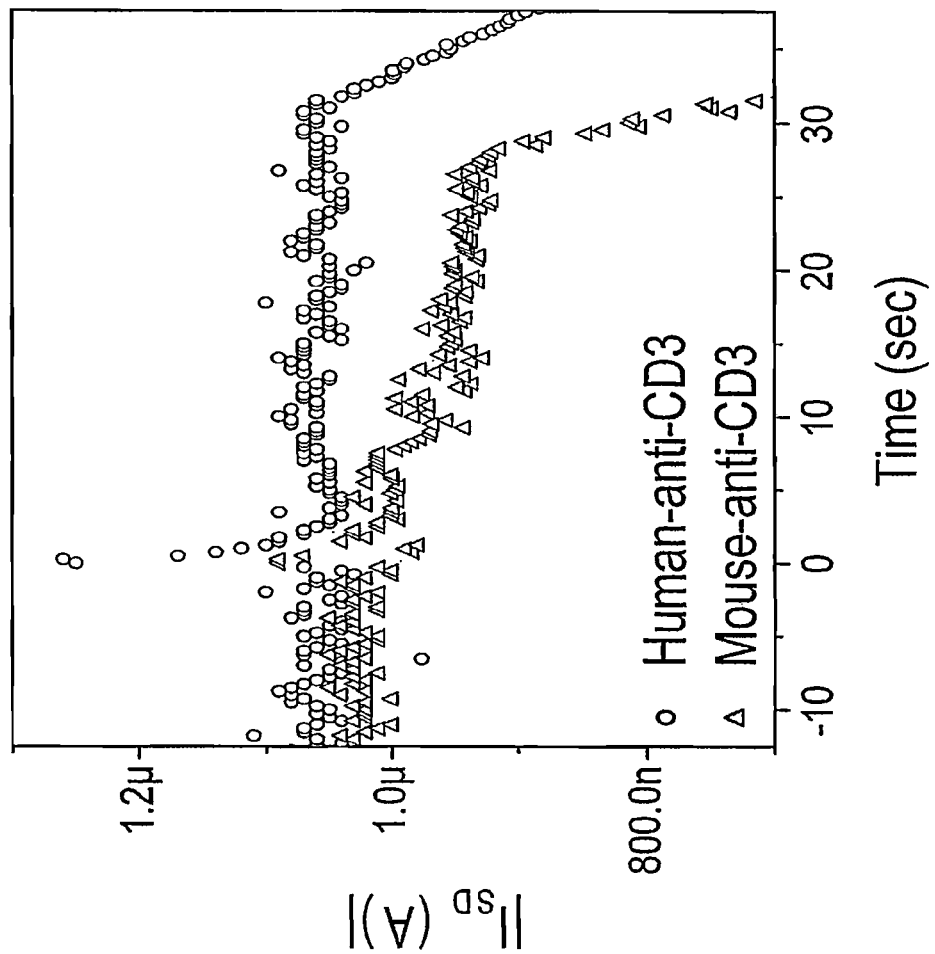
FIG. 9 illustrates conduction current responses in biotin-functionalized p-type nano-wire sensors to the addition of human-α-3 and mouse-α-3 stimulants.

As described above, unfunctionalized nano-wire devices may act as ion sensors for sensing pH and other ionic changes of substances disposed on its native oxide surface. In one embodiment, such unfunctionalized nano-wire devices are used to monitor real-time cellular responses of activation-induced changes in extracellular pH. For example, real-time T-lymphocyte activation may be monitored using a nano-wire sensor, where the T-cell activation may be triggered by antibody-mediated crosslinking of cell-surface CD3, which induces intracellular signaling and, subsequently, engages effector mechanisms. One consequence of such activation includes the release of acid that alters the surface charge density of the sensor. In one illustrative implementation, a species-specific antibody directed against mouse CD3 complex (mouse-α-3) is added to a suspension of mouse splenocytes containing about 6000 mouse-derived T-cells. This solution is then introduced to a nano-sensor, having a cross-sectional width of about 100 nm and a cross-sectional thickness of about 40 nm, to detect T-cell activation by the mouse-α-3 stimulant. As illustrated in FIG. 9, the subsequent decrease in extracellular pH caused by the T-cell activation corresponds to an approximate 7.3% decrease in average current measured by the nano-sensor after a current baseline is established for about 10 seconds. This current continues to decrease until current instability occurs after about 30 seconds of sensing.

In another illustrative implementation, an antibody specific to human CD3 (human-α-3-CD3) complex, which does not bind to mouse CD3, is added to the same suspension of mouse splenocytes as described above. Hence no mouse-derived T-cell activation is expected to take place. This is confirmed by electrical current measurements taken from the sensor device, as shown in FIG. 9, which indicates that minimal change in current has resulted from the addition of the human-α-3-CD3 stimulant.

Figure 10:
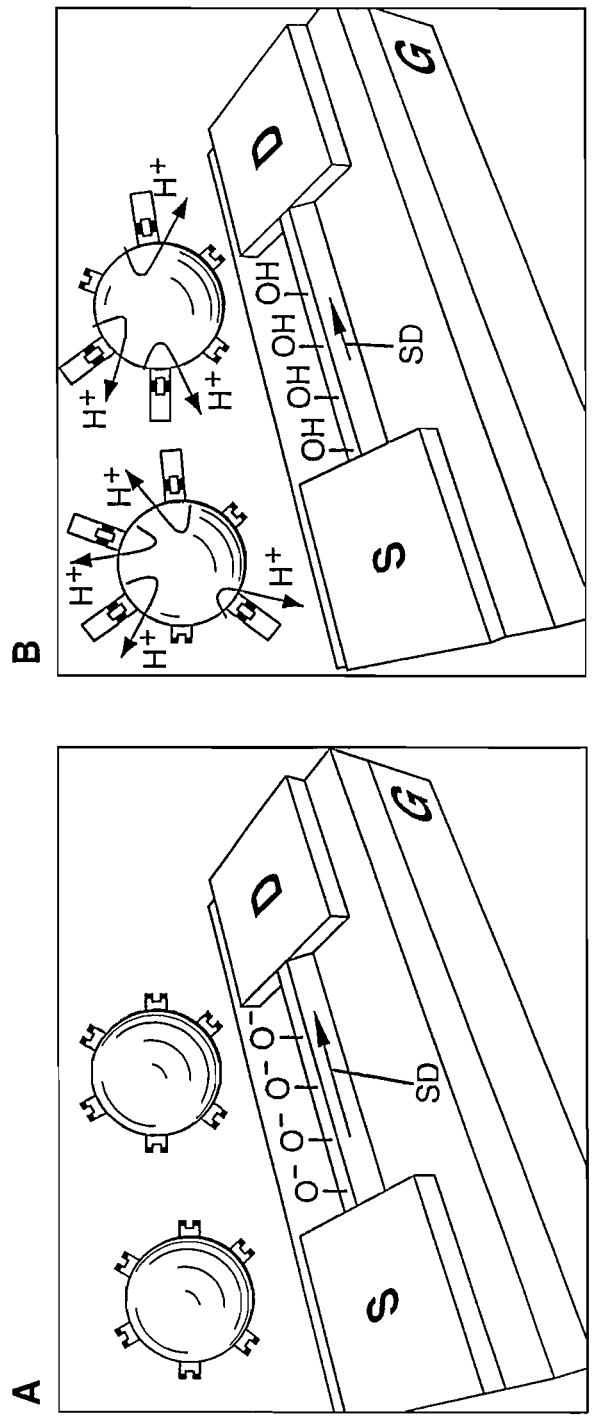
FIG. 10A depicts a sensing schematic prior to T cell stimulation. Prior to T cell activation, a majority of the nanowire's silanol groups (active region colored black) are deprotonated.
FIG. 10B depicts a sensing schematic post T-cell stimulation. After stimulation+activation, extracellular acidification results in increased protonation of the surface silanol groups, which decreases $I_{SD}$.

Yet other illustrative embodiments may be useful for sensing certain aspects of proton secretion due to activation-induced polyclonal T-cell signaling. FIGS. 10A and 10B shows a sensing schematic: pre-T cell stimulation and post-stimulation+activation, respectively. Prior to T cell activation, a majority of the nanowire 20 silanol groups are deprotonated. After activation, extracellular acidification results in increased protonation of the surface silanol groups, which would decrease $I_{SD}$. The time required for T cell activation after stimulant addition can be quantified.

Figure 11:
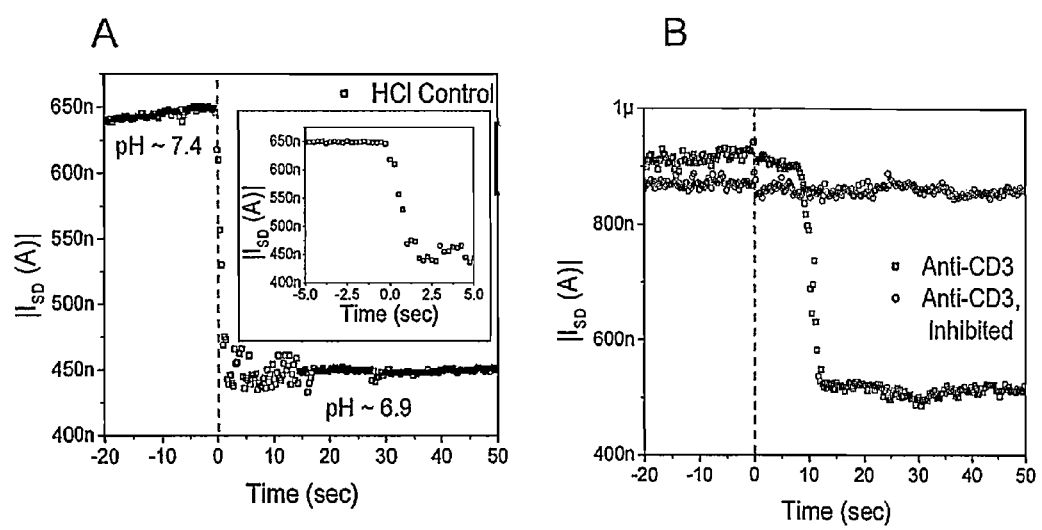
FIG. 11A shows device response to the addition of 1 mL of dilute hydrochloric acid to a cell-free buffer, demonstrating system response of approximately 1.5 sec.; Solution pH values are also provided.
FIG. 11B shows measurement of extracellular acidification upon stimulation of B6 splenocytes with anti-CD3. The T cell response time is approximately 8 sec. Pre-treatment of splenocytes with genistein (50 mg/mL), which inhibits cell signaling, eliminates anti-CD3 induced cellular metabolic activity.

For example, splenocytes isolated from a C57BL/6 (B6) mouse were suspended in a low-buffered solution and stimulated with anti-CD3 antibody. FIG. 11B shows that extracellular acidification was observed to begin approximately 8 sec after injection. Without being limited by theory, approximately 8 sec delay observed in FIG. 11B was believed to be primarily due to intrinsic cellular processes. To ensure that extracellular pH changes were due to stimulation-induced cellular metabolic activity, splenocytes derived from the same mouse were treated with genistein, an antibiotic that inhibits the induced intracellular signaling cascade, without affecting cellular viability. FIG. 11A shows that the presence of genistein, addition of anti-CD3 antibody resulted in no change in solution pH. This confirmed that the positive response observed in untreated cells was due to anti-CD3 antibody-initiated proton secretion from splenocytes.

Figure 12:
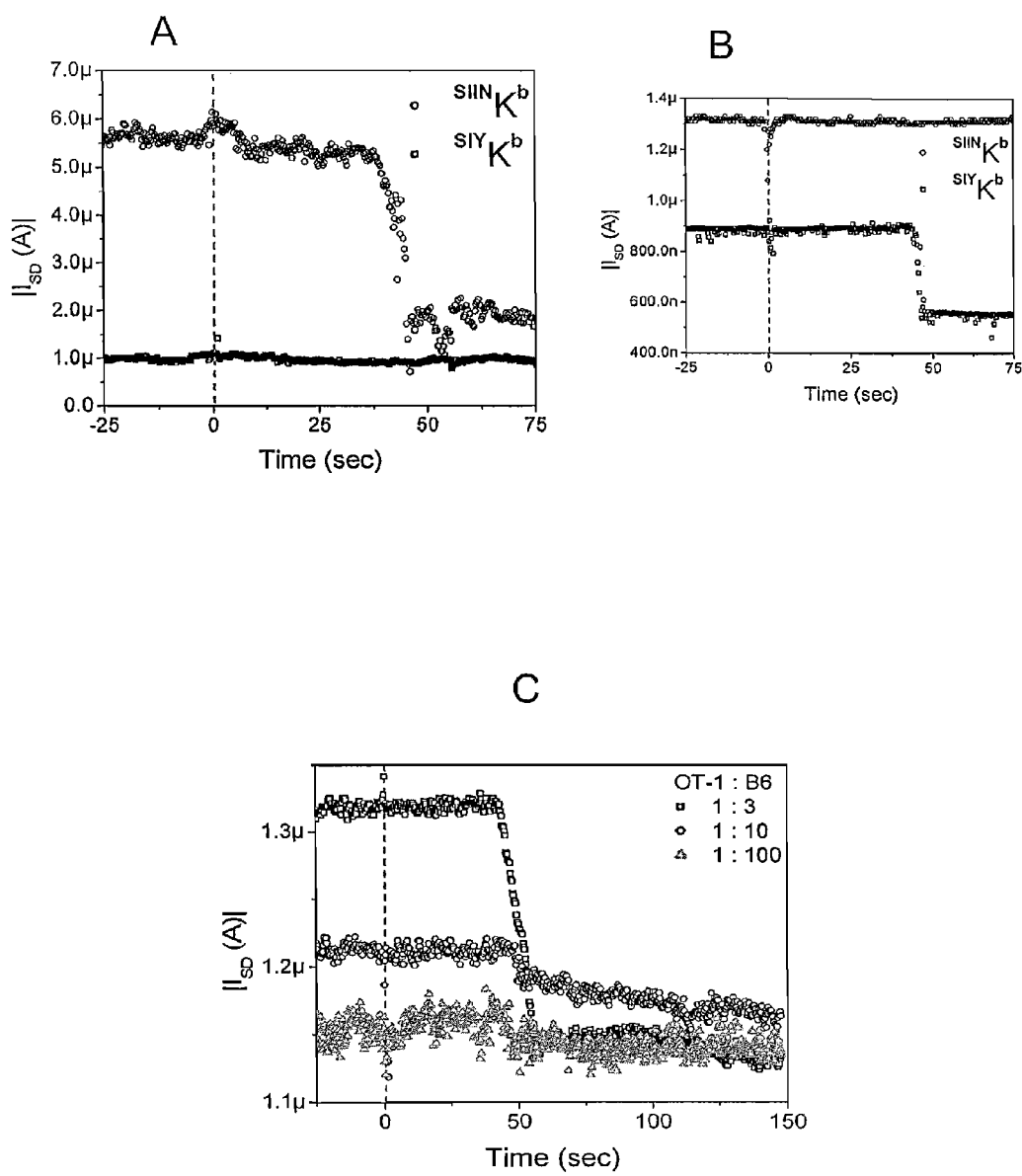
FIG. 12A shows OT-1 stimulated with $^{SIIN}K^b$ and $^{SIY}K^b$ dimeric constructs. Extracellular acidification began at approximately 40 sec for the positively-stimulated splenocyte population.
FIG. 12B shows 2C splenocytes stimulated with $^{SIIN}K^b$ and $^{SIY}K^b$ dimeric constructs. Extracellular acidification began at approximately 40 sec. for positively-stimulated splenocyte population.
FIG. 12C shows OT-1 splenocytes diluted to various ratios with wild-type B6 splenocytes; CTL. The response to stimulation with $^{SIIN}K^b$ was measured.

Still other embodiments were are suitable for discriminating between well-established peptide-specific MHC restricted responses of T-cell clones. For example, murine splenocytes isolated from 2C and OT-1 transgenic mice were stimulated with dimeric MHC ligands presenting their cognate and non-cognate peptides. 2C and OT-1 CD8$^+$ T-cells (cytotoxic T-lymphocytes, CTLs) react against a broad range of defined peptides presented by syngeneic MHC Class I, H-2K$^b$. OT-1 mice, expressing a transgene for the T-cell antigen receptor, are reactive with the complex of H-2K$^b$ and the ovalbumin octapeptide SIINFEKL ($^{SIIN}$K$^b$). As a negative control for this system, the inventors used a non-cognate peptide derived from a peptide library, SIYRYYGL ($^{SIY}$K$^b$). Cytotoxic T-lymphocytes from 2C transgenic mice should be reactive to $^{SIY}$K$^b$ but exhibit a null response to $^{SIIN}$K$^b$). Using a NW-FET sensor of the present invention, a drop in solution pH beginning approximately 40 sec after addition of $^{SIIN}$K$^b$ dimer to OT-1 splenocytes was observed; no response was observed after addition of $^{SIY}$K$^b$ (FIG. 12A). Conversely, 2C CTLs reacted to the presence of the $^{SIY}$K$^b$, with proton secretion beginning approximately 40 sec after peptide/MHC addition. The device showed no discernable changes in conductance when $^{SIIN}$K$^b$ was added to 2C splenocytes (FIG. 12B).

The observed onset of extracellular acidification of T-cells upon stimulation with peptide/MHC, after a lag of approximately 40 sec, was longer than that measured for anti-CD3 antibody stimulation, the approximately 8 sec. There were believed two candidate mechanisms potentially responsible for the observed delay: 1) the kinetics of T-cell activation are strongly affected by the dwell time of the T-cell receptor-activating stimulus. Antibodies that trigger the CD3 complex bind with higher affinities ($K_d$ approximately 1-10 nM) than peptide/MHC complexes ($K_d$ approximately 1-100 µM), which may lead to faster intracellular signaling, resulting in earlier acid release. 2) A smaller population of responsive cells (typically approximately 20-30% of all transgenic splenocytes are reactive to the specific antigen) may require a longer time for accumulation of the signaling molecules needed to achieve sufficient extracellular acidification.

Stimulating dilutions of OT-1 cells mixed with background splenocytes derived from B6 mice was used to distinguished between these possible mechanisms. Upon stimulation with cognate antigen ($^{SIIN}$K$^b$), FIG. 12C shows a decrease in device signal intensity with decreasing numbers of OT-1 cells. The observed responses were produced by OT-1 splenocyte populations of approximately 28000, 7000, and 700 cells for the 1:3, 1:10, and 1:100 dilutions, respectively. The onset of stimulus-induced extracellular acidification began approximately 45-49 sec for all dilutions, indicating that the strength of the stimulus, rather than changes in the cell density, was responsible for the delay. These data are consistent with previous studies that monitored the dynamics of intracellular calcium flux (which had similar response times) after stimulation with different agonists and showed that the apparent lag time after antigen-specific T-cell triggering correlated with signal strength.

These, and still other, exemplary embodiments illustrate that the nano-sensors of the present invention are suitable for the accurate and efficient monitoring of real-time cellular responses based on sensing activation-induced changes without tagging or labeling the pertinent reagents involved in the reactions. The enhanced device sensitivity also contributes to the efficiency with which detections are enabled. Indeed, such illustrative nano-sensor are suitable for label-free detection of stimulus-induced extracellular acidification within seconds after stimulation of a small number of cells, <210 (30% of 700). Illustrative NW-FET sensor sensitivity, rapid response time, low required sample volume, and suitability for high-throughput analysis show great applicability towards a variety of clinical and diagnostic applications.

Nano-sensors of the present invention, and their associated methods of use, may be used in diagnostic applications that require the accurate discrimination among cells primed against different pathogens. For example, HIV infected cells (lymphocytes) respond to HIV antigens via activation-induced changes in T-cell functions. Thus, lymphocytes isolated from healthy and diseased donors who are non-responsive and responsive, respectively, to HIV antigens can be easily and quickly screened in a label-free manner using the sensor device of the present invention.

Unfunctionalized nano-sensors may also be used to monitor other real-time cellular responses based on the sensing of activation-induced extracellular ionic changes. For example, the nano-sensor devices may be used to detect the stimulation of T-cells, neutrophil, basophil, dendritic, macrophage, regulatory and natural killers, and other cells of the immune system. In these applications, stimuli of the respective cells are used to discriminate among the cells primed against specific antigens. Each interaction is likely to trigger extracellular changes in ions that are detectable by the sensor device due to a correlated change of the device conduction current. Exemplary ionic changes include changes related to hydrogen ions, calcium ions, ATP ions, and other ions that tend to propagate during cellular responses. Exemplary stimuli include antibodies, peptide or major histocompatibility complexes, carbohydrates, nucleotides, synthetic polymers and monomers, and other ligands that tend to trigger cellular functions.

In yet another application, unfunctionalized nano-sensor devices may be used to ascertain protein and macromolecule stability and aggregation potential because as these molecules unfold, for example, upon exposure to a denaturant, the molecules tend to change the electrical properties of the nano-sensor whereon the molecules are applied. The resulting change in device conduction current can be used to deduce a stability measurement for each molecule, hence providing a facilitated approach to assess the propensity of the molecule towards aggregation which potentially leads to one or more diseased states. For example, detection of unfolding and aggregation of amyloid peptides may be a warning sign for Alzheimer's. Detection of crytallin peptide aggregation may be a warning sign for cataracts.

In another application, the nano-wire sensors may be used to detect exocytosis, which is essential to normal cell functions and forms the basis of intercellular communication in multi-cellular organisms. Exocytosis involves the intracellular and intercellular transport of membrane-bound vesicles that tend to release their content upon fusion with other cells. Hence, the sensor device of the present invention may be used to detect exocytosis by sensing changes in the device's electrical properties in correlation to degranulation, or the release of substances, from the vesicles. Secreted substances include proteins, carbohydrates, ions, nucleotides or other macromolecules with a net surface charge that impacts the charge of the sensor. More specifically, the sensor device is able to detect pathological cells in connection to two known types of exocytosis. Constitutive exocytosis occurs independent of extracellular stimuli. Often, this type of exocytosis is dysfunctional in diseased or infected cells. Therefore, the ability to monitor constitutive exocytosis is important to differentiating between normal and pathological cells without the presence of a stimulus. Regulated exocytosis occurs when cells are triggered by a stimulus which may lead to secretion of hormones, acidic granules, second messengers, digestive enzymes and other molecules. Again, dysfunction in regulated exocytosis may be indicative of pathology. Often, pathological cells secrete granules in response to external stimuli such as the way HIV-infected cells respond to HIV antigens or autoimmune cells respond to autoimmune antigens. The sensor device is able to measure exocytic secretion of granules resulted from both constitutive and regulated exocytosis. In addition, the sensor device is able to distinguish between cells capable and incapable of secreting granules. In certain exemplary applications, exocytosis in neurons, endocrine neurons, neuroendocrine/endocrine cells, exocrine cells and hemopoietic cells are detected by the sensor devices based on their secreted granules which tend to alter the electrical properties of the devices. These secreted granules include, for example, dense-core vesicles, chromaffin granules, secretory granules, mucin granules, lamellar body, zymogen granules, casein vesicles, lysosome-related granules and other molecules.

In yet another application area, the nano-wire device of the invention is able to distinguish between apoptotic and non-apoptotic cells, which is critical to discriminating between pathological and non-pathological states in many types of cancer as well as to the detection of autoimmune and alloimmune disease states. In general, dying cells that undergo the final stages of apoptosis rearrange the cell surface and certain phospholipids on the cell surface. For example, phosphatidylserine that are normally found on cytosolic (inner) surface of a plasma membrane are redistributed during apoptosis to the membrane's extracellular surface. Because cell membranes are typically negatively charged, apoptosis results in a reduction of the overall charge which impacts device electrical properties upon the introduction of the cells onto the device surface. In many cases, this reduction of charge is in addition to an overall degranulation and secretion of cytoplasmic factors that take place during the apoptotic process.

According to another aspect of the invention, in addition to using unfunctionalized sensor devices to monitor real-time cellular responses, the detection capability of the nano-sensor may be expanded via selective sensor surface functionalization which permits sensing of desired ions in addition to protons as well as sensing of disparate indicators for a variety of cellular assays. For example, a nano-sensor may be functionalized by receptor molecules that bind to specific reagents, in which case a conductance change occurs in the corresponding sensor device. Given a p-type nano-wire, its conductance is adapted to increase when a macromolecule with negative surface charge binds to a nano-wire surface functionalized with receptor molecules, whereas the opposite response occurs when a positively-charged molecular binding occurs on a functionalized device surface. Hence functionalized nano-wires are well suited for performing selective label-free sensing of macromolecules. In addition to p-type nano-wire functionalization, selective n-type nano-wire functionalization is equally viable for performing label-free sensing. Details regarding n-type nano-wire sensors will be described below.

Some functionalization methods, such as hydroxyl-reactive schemes, require the functionalization of the entire sensor surface, including the underlying oxide, which diminishes sensitivity of the nano-sensor due to binding competition. Thus, selective device functionalization is critical to the retention of sensitivity. A selective device functionalization process is provided according to an embodiment of the present invention, according to which nano-wires are introduced into an inert $N_2$ atmosphere, etched for about 5 seconds in 10:1 buffered oxide etch, rinsed and dried, coated with a functionalizing solution, and subjected to about a 2 hour UV treatment. Deprotection may be performed with 25% TFA in methylene chloride utilizing any prior art procedure. After washing and deprotecting, the yield of the device for effective selective functionalization is less than about 2%.

Dec-9-enyl carbamic acid tert-butyl ester may be used to functionalize nano-sensor devices because this substance has been shown to confer amine functionality. Dec-9-enyl carbamic acid tert-butyl ester may be synthesized using any prior art procedure. This molecule is the same as 10-N-boc-amino-dec-1-ene, which has been shown to selectively functionalize silicon-over-oxide. All chemicals required for synthesizing dec-9-enyl carbamic acid tert-butyl ester may be purchased from Sigma-Aldrich. H NMR (500 MHz, $CDCl_3$) δ 5.79 (1H, ddt, J=17, 10.2, 6.7 Hz, CH), 4.98 (1H, dd, J=17, 1.7 Hz, CH), 4.91 (1H, dd, J=10.2, 1.7 Hz, CH), 4.88 (1H, s, NH), 3.09 (2H, m, $CH_2$), 2.03 (2H, m, $CH_2$), 1.47-1.29 (12H, m, $CH_2$), 1.44 (9H, s, $CH_3$); $_{13}C$ NMR (500 MHz, $CDCl_3$) δ 156.06, 138.98, 114.20, 78.68, 40.62, 33.80, 30.12, 29.43, 29.29, 29.06, 28.92, 28.46, 26.83.

Figure 13:
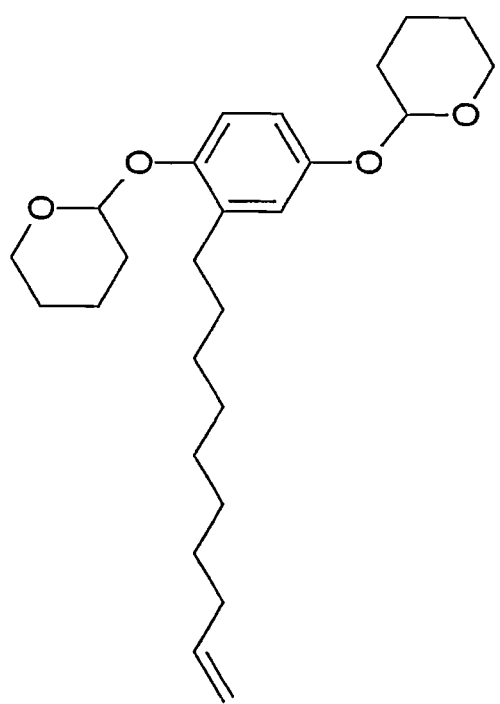
FIG. 13 illustrates an exemplary 2-[4-(tetrahydro-2H-pyran-2-yloxy) phenoxy]tetrahydro-2H-pyran molecule.

Another functionalization substance may be 2-[2-(undec-10-enyl)-4-(tetrahydro-2H-pyran-2-yloxy) phenoxy]tetrahydro-H-pyran. This molecule, whose structure is shown in FIG. 13, may be synthesized from 2-[4-(tetrahydro-2H-pyran-2-yloxy) phenoxy]tetrahydro-2H-pyran using any prior art process. The intermediate may be synthesized by first adding dihydropyran (0.83 mL, 9.1 mmol) and pyridinium p-toluenesulfonate (0.11 g, 0.45 mmol) to a solution of hydroquinone (0.25 g, 2.3 mmol) in $CH_2Cl_2$ (3 mL). This reaction mixture is then stirred for about 12 hours and diluted with 10 mL of $CH_2Cl_2$. The mixture is subsequently washed by 3×5 mL of $NaHCO_3$ and 1×5 mL brine, dried over $MgSO_4$, and concentrated to a white solid. Silica gel chromatography (4:1 hexane/ethyl acetate) provides the di-tetrahydropyran hydroquinone as a white solid (0.48 mg, 75%).

In certain embodiments, optimal device operation regions are determined for nano-sensors selectively functionalized with each of the aforementioned substances. After device functionalization and deprotection with dec-9-enyl-carbamic acid tert-butyl ester, as shown in FIGS. 14A and 14B, respectively, absence of device pinch-off is observed for source-drain voltages $V_{SD}$ that are less than about −5V (−$V_{SD}$>5V), hence suggesting a possible occurrence of parallel conduction at high bias through the functionalization layer which induces the creation of alternative conduction paths. However, at $V_{SD}$ greater than about −5V (−$V_{SD}$<5V), the current leakage is negligible and the device is well suited for sensing. Thus, for certain functionalized nano-sensor operations, the $V_{SD}$ is maintained at −2V or above for optimal sensing. Similar device operation regions may be applied to devices functionalized with 1-decene, whose conductivity response is shown in FIG. 14C. In certain implementations, dec-9-enyl-carbamic acid tert-butyl ester and 1-decene are preferred as functionalization substances over 2-[2-(undec-10-enyl)-4-(tetrahydro-2H-pyran-2-yloxy) phenoxy]tetrahydro-H-pyran because the latter substance may destroy the gating behavior of some nano-wire devices.

Functionalized nano-sensors may be used to detect certain macromolecules based on selective protein binding. According to one example, electrical responses of biotin-functionalized device to the addition of 1 nM streptavidin, 1 nM biotin-quenched streptavidin, which is streptavidin pre-treated with 5 equivalents of biotin, and 1 nM avidin are determined. In order to avoid the problem of Debye screening, the salt concentrations in the buffers used for macromolecular sensing are chosen such that the Debye screening length ($\lambda_D$) is long enough not to impede sensing, but short enough that unbound macromolecules are screened. As shown in FIG. 15A, addition of a streptavidin solution results in a current increase in the nano-sensor due to the protein's negative charge, hence demonstrating selective protein recognition and the dependence of device electrical signal on protein charge. The inset 1202 of FIG. 15A depicts an exemplary fluorescence micrograph image of a biotin-functionalized device having a width of about 500 nm and a thickness of about 40 nm that is treated with 1 nM of AlexFluor 655-linked streptavidin. However, addition of biotin-quenched streptavidin to a biotin-functionalized nano-wire sensor elicits no response as demonstrated by the minimal fluctuation observed in the measured current shown in FIG. 15A. However, device current noticeably drops upon introduction of avidin, having an isoelectric point (pI) of about 0.5, due to avidin's positive charge. In additional examples of selective functionalization, a poly(ethylene glycol) (PEG) functionalized device yields no conduction response to an addition of 1 nM streptavidin (pI about 5.6), which is also illustrated in FIG. 15A.

According to another embodiment, functionalized nano-sensors are capable of reversing sensor responses to the addition or removal of reagents. In one exemplary implementation, the reversibility of sensor response to streptavidin addition and removal is demonstrated. Biotinylation, or biotin functionalization, of a single sensor is performed with a cleavable molecule SS-biotin, which may be processed from sulfo-NHS-biotin with a 2.4-nm linker having a dithiol bond. A second sensor is biotinylated with a noncleaving molecule LC-biotin that may be processed from sulfo-NHS-biotin with a 2.2-nm PEG linker. The response of each sensor to 1 nM streptavidin addition is similar, as illustrated in FIG. 15B. Subsequently, a reducing agent, tris(2-carboxyethyl)phosphine (TCEP), is added to the nano-sensor, as shown by the arrow 1204 of FIG. 15B. The addition of the reducing agent cleaves the disulfide bond between the SS-biotin and the streptavidin which subsequently reverses the sensor response to baseline current. However, the LC-biotin control, which does not cleave disulfide bonds, is insensitive to the reducing agent and produced minimal response.

Molecular charge screening by dissolved solution counterions—Debye screening—on sensor response may evaluated. Certain embodiments of the present invention were functionalized with APTS to effect amine-modified surfaces in high yield (>90%). Conventional shortcomings of the APTS technique—that essentially the entire NW-FET would be functionalized with amines—are thought to dramatically decrease sensing device sensitivity. Accordingly, certain preferred functionalized embodiments of the present invention were pattered to provide a final photoresist layer that exposed only a small region around the active devices as depicted by FIG. 3A.

Figure 16:
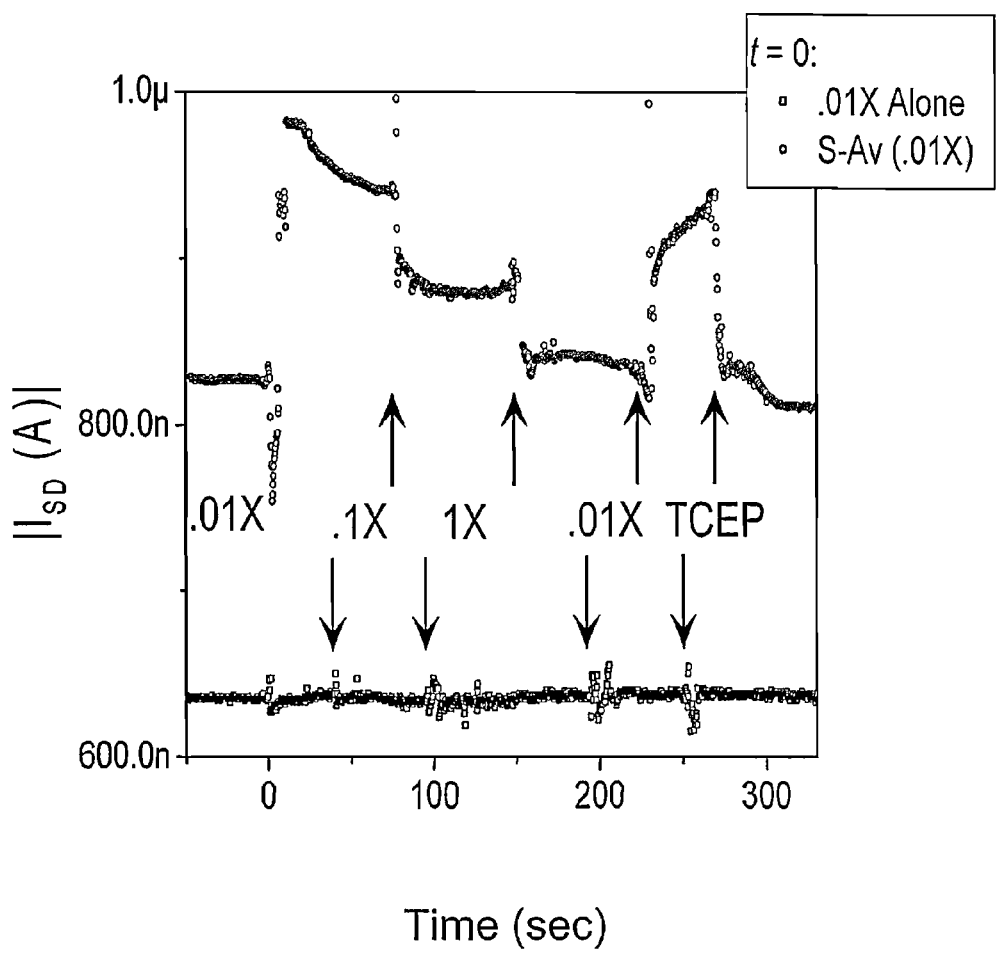
FIG. 16 shows biotin-functionalized sensor response (|$I_{SD}$| vs. time) to varying buffer ionic concentrations with, and without, streptavidin addition at time=0.

Next, the effect of increasing buffer ionic strengths (decreasing Debye length—$\lambda_D$) on device recognition sensitivity was determined. A NW-FET device, of the present invention, was functionalized with a cleavable biotin molecule and, after establishing a baseline current in 0.01×PBS, 10 nM streptavidin was added in the same buffer. The binding of streptavidin, a negative protein with an isoelectric point (pI) of approximately 5.6, to the biotinylated device resulted in an increased. $I_{SD}$, of the p-type device (FIG. 2B). The ionic strength of this buffer yields a $\lambda_D$ of approximately 7.3 nm. Thus the majority of the protein's charge is unscreened at the NW-FET surface (FIG. 16B). A ten-fold increase in the ionic strength of the buffer (0.1×PBS, $\lambda_D$ approximately 2.3 nm) partially screens streptavidin's intrinsic charge and a further ten-fold increase in buffer ionic strength (1×PBS, $\lambda_D$ approximately 0.7 nm) effectively screens most of the protein's charge, returning the $I_{SD}$ approximately to its baseline value (FIG. 16B). The device current level begins to recover to its 0.01×PBS value after a subsequent decrease in ionic strength by solution exchange with this buffer. The addition of the reducing agent tris(2-carboxyethyl)phosphine hydrochloride (TCEP), which cleaves the biotin linker and, thus, removes streptavidin from the sensor surface, returns $|I_{SD}|$ to its original baseline level, see FIG. 16B. As a control, the same series of solution exchanges was applied to a nominally identical biotinylated device using streptavidin-free buffers (FIG. 16B). The absence of a change in signal demonstrates that the NW-FET response is independent of ionic strength (e.g., $\lambda_D$).

Figure 17:
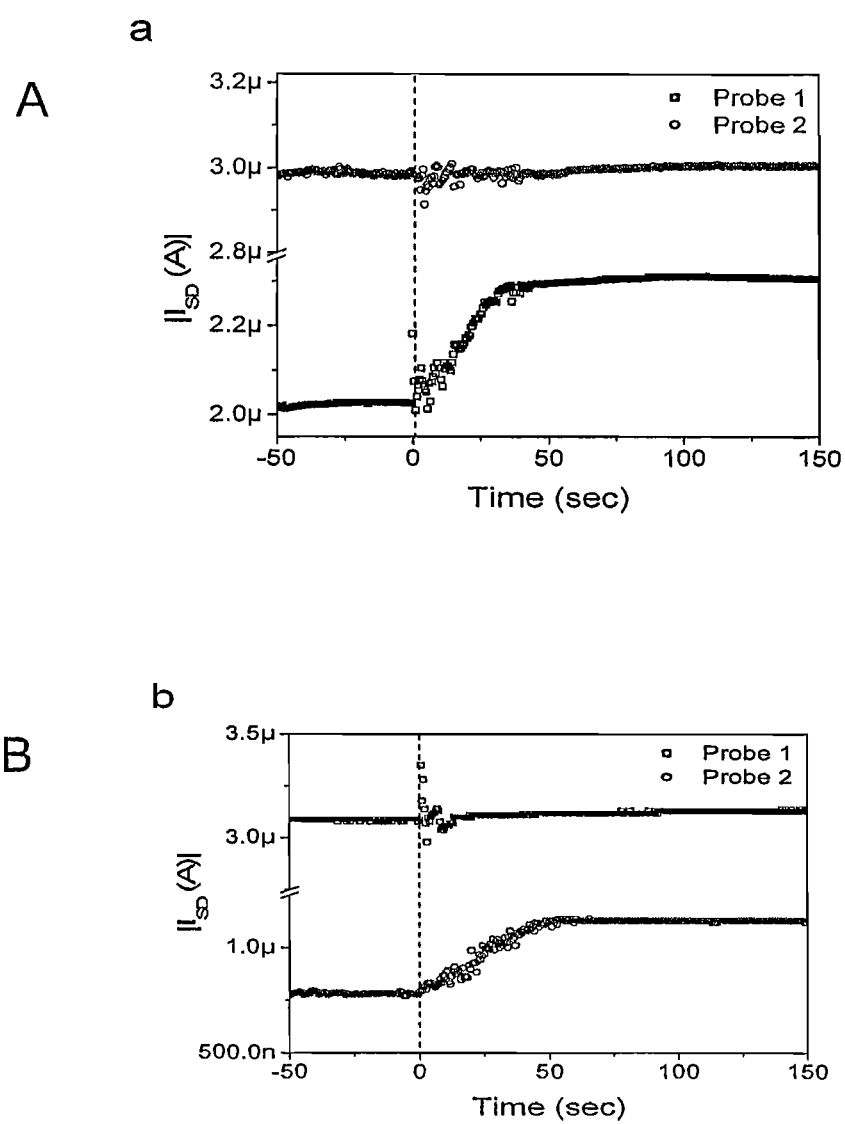
FIG. 17A shows the response of NW-FETs functionalized with the Probe 1 DNA strands to the addition of 10 pM solutions of target DNA strands. Solution exchange occurs at time=0, highlighted by the dashed line.
FIG. 17B shows the response of NW-FETs functionalized with the Probe 2 DNA strands to the addition of 10 pM solutions of target DNA strands. Solution exchange occurs at time=0, highlighted by the dashed line.

For yet other certain preferred embodiments, cross-comparison assays were performed to determine device suitability for specific ssDNA strand recognition. For example, two exemplary NW-FET devices were functionalized with the DNA-P(1) sequence and two devices with the DNA-P(2) sequence. All such devices having a Debye length ($\lambda_D$) of about 3.3 nm relative to the NW-FET sensor surface. Under active measurement conditions (VSD=−2V, VGD=−35V) and after the establishment of a baseline signal in 0.05×PBS, the solution was exchanged with 10 pM solutions of target DNA, either DNA-T(1) or DNA-T(2), in the same buffer. FIGS. 17A and 17B show the responses of the DNA-P(1)- and DNA-P(2)-functionalized devices, respectively, to DNA-T(1) and DNA-T(2). In both cases, complementary pairing results in an increase in $|I_{SD}|$, as expected for a p-type device, while the noncomplementary negative controls show little change in signal, indicating a buffer with an optimal $\lambda_D$. The near-negligible signal of the negative controls indicates the $\lambda_D$ of about 3.3 nm effectively screens unbound DNA.

These results demonstrate the importance of selecting a buffer with an appropriate $\lambda_D$ to ensure proper NW-FET sensing. Careful control of the solution Debye length ($\lambda_D$) ensures that specific binding of macromolecules contribute to sensor response. An autonomous system for analyte detection must properly take these issues into account, such as employing ionic strength feedback control. This demonstration also profiles an application where charge distribution may enable unique measurements of the configuration of surface-bound species.

Figure 18:
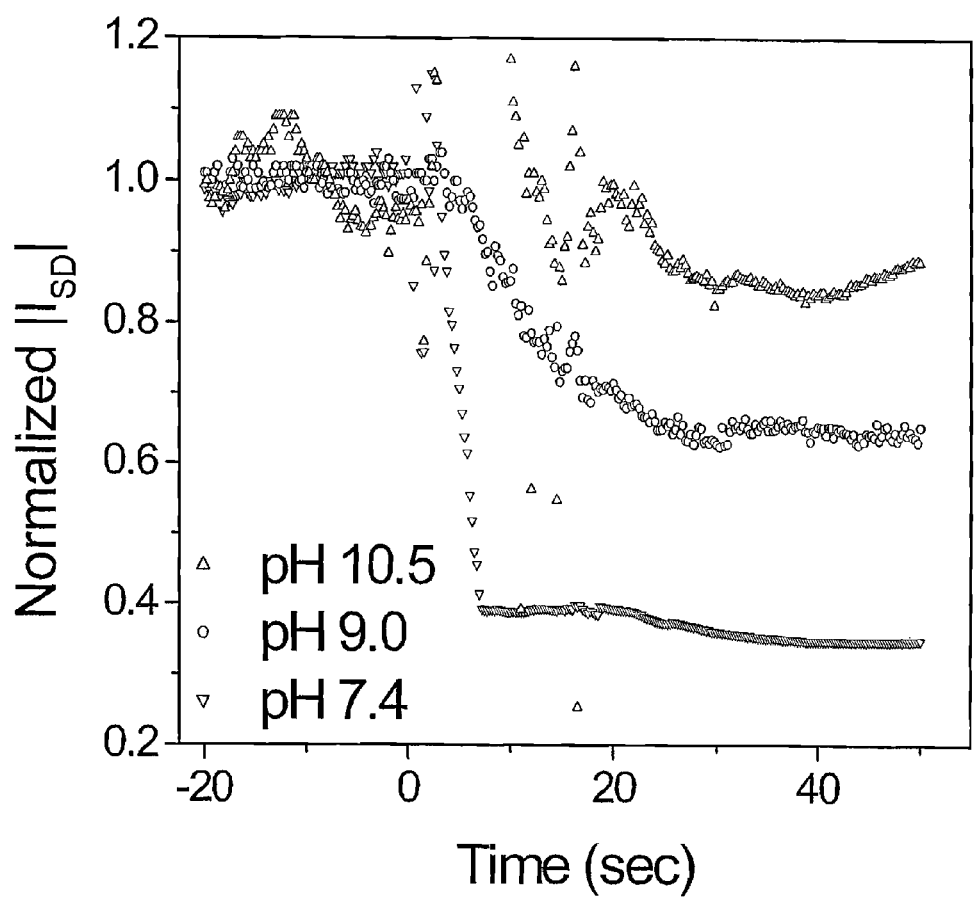
FIG. 18 demonstrates device sensitivity of biotin-functionalized p-type sensors to the addition of advin solutions with varying pH.

Protein sensing ability of the functionalized nano-sensor devices may be optimized with regard to its sensitivity to protein charge and concentration, according to another embodiment of the invention. This determination is made based on measured conductivity response resulting from the introduction of three solutions with varying pH to a biotinylated nano-sensor, where each solution includes 1 nM of avidin and an appropriate pH buffer. Even though avidin is positive in neutral solutions due to its high isoelectric point (pI about 10.5), its effective charge may be decreased by the increase in solution pH. FIG. 18 demonstrates decreased device sensitivity in correlation to increased solution pH. Hence, the value of $|pH_{solution}-pI|$ needs to be maximized to optimize protein sensing. In other implementations, protein sensing is optimized by the use of a linear solution pH gradient to determine unknown protein pIs.

In general, 0.1×PBS having pH of 7.4 may be utilized for biotin-streptavidin/avidin sensing, where the 0.1×PBS has a Debye screening length ($\lambda_D$) of about 2.2 nm. Despite the fact that calculating the actual amount of protein captured and sensed has inherent uncertainties, about 7 fg of protein is estimated to bind to a single sensor, assuming that the sensor has a cross-sectional width of about 100 nm and a cross-sectional thickness of about 40 nm, and the protein concentration is about 1 avidin molecule/25 $nm^2$. In addition, Biotinylation may be performed with N-hydroxysulfosuccinimide (sulfo-NHS)-biotin, sulfo-NHS-SS-biotin, or sulfo-NHS-LC-biotin (Pierce Chemical) at pH of 10.5.

Figure 19:
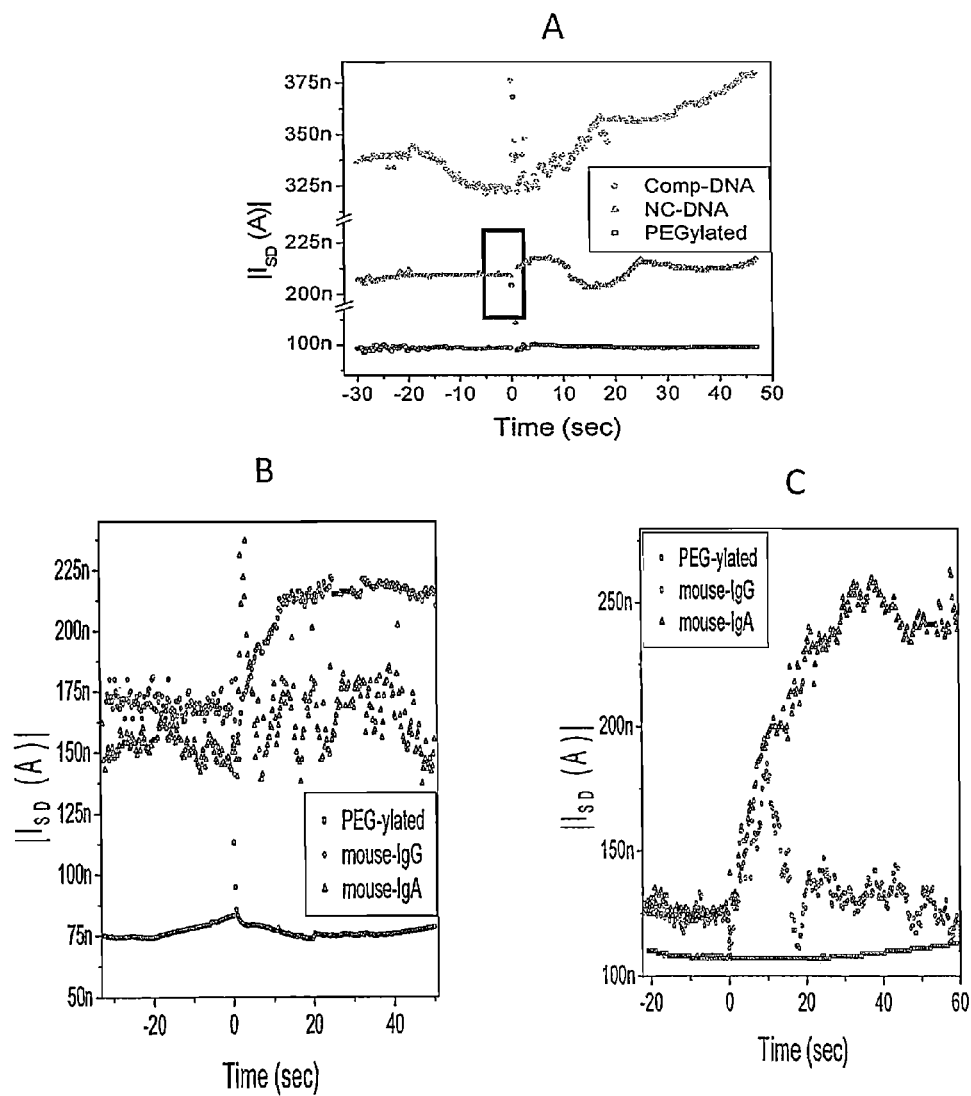
FIG. 19A illustrates current responses in DNA-functionalized p-type sensors to the addition of a complementary and a non-complementary 15-mer concentration.
FIG. 19B-19C illustrate current responses in a goat-α-mouse IgG functionalized p-type sensor and a goat-α-mouse IgA functionalized p-type sensor to the introduction of mouse IgG and mouse IgA, respectively.

Selectively functionalized sensor devices may also be utilized in the detection of complementary DNA, as shown in FIG. 19A. In particular, two exemplary sensor devices are functionalized with a 20-mer, 5'-thiol ss-DNA, with subsequent introduction of either a complementary or a non-complementary 15-mer at a 100 fM concentration on each device. The sensor response to complementary strand addition is observed to be more than the non-complementary strand addition.

In another embodiment as shown in FIGS. 19B and 19C, a protein assay is performed by functionalizing two devices with goat-α-mouse IgG and two additional devices with goat-α-mouse IgA. One device from each group is used to sense the presence of mouse IgG and the other mouse IgA, where both solutions have about 100 fM concentrations. Sensing is subsequently performed at pH of 8.5 to maximize protein charge while maintaining protein conformation. As seen in FIGS. 19B and 19C, the appropriate ligand is detected in each case, while current in non-immune devices remained relatively constant. Thus, the ability of this functionalization approach for the detection of antibodies at less than about 100 fM concentrations is demonstrated. In certain examples, the captured antibodies are bound using NHS/ethylene dicarbodiimide coupling techniques. The sensing may be performed in a 1 mM sodium bicarbonate buffer, having pH of 8.4 and Debye screening length ($\lambda_D$) of about 6.8 nm.

The functionalized nano-wire sensors used in the aforementioned implementations may be nominally similar, with device cross-sectional thickness about 40 nm and device cross-sectional width varies from about 50 nm to about 150 nm.

According to another aspect of the invention, the nano-sensor devices, whether functionalized or unfunctionalized, are used for complementary sensing. N-type inversion-mode devices may be fabricated on the same wafer as p-type accumulation-mode devices to support the complementary sensing ability. An $I_{SD}$, ($V_{SD}$) dependence plot, with $V_{GD}$ varying from 0 to 40V in 1V increments, is shown in FIG. 6B for an exemplary n-type sensor device having a width of about 50 nm and a thickness of about 40 nm. The $I_{SD}$, ($V_{GD}$) dependence plot for $V_{SD}$=1V is shown in the inset of FIG. 6B. As with the p-type $I_{SD}$ ($V_{GD}$) behavior illustrated in FIG. 6A, the small hysteresis between forward and reverse $I_{SD}$, ($V_{GD}$) slopes in the inset in FIG. 6B suggests minimal defect-induced charge trapping in the n-type nano-wire sensor device. The observed n-type behavior is possibly due to the polarity of the contacts to the device, which may be controlled by contact implantation or physical definition. For simplicity, surface accumulation charge caused by ME pattern definition may be used, which is sufficient to invert the contact, thereby decreasing the contact resistance and enabling inversion-mode behavior. This results in ambipolar behavior, as evident in the inset of FIG. 6B. The n-type and p-type nano-wire sensors may be incorporated into an integrated electronic system to perform functions such as on-chip signal processing, error detection, and complementary error detection for the purpose of avoiding false positives.

Figure 20:
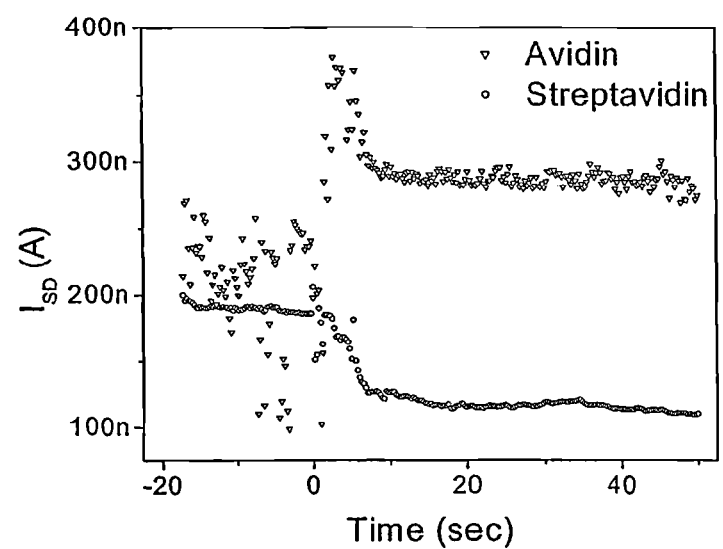
FIG. 20A illustrates conduction current responses in biotin-functionalized n-type sensors to the introduction of streptavidin and avidin.
FIG. 20B illustrates current responses in a goat-α-mouse IgG functionalized n-type sensor to the addition of mouse IgG.
Figure 20:
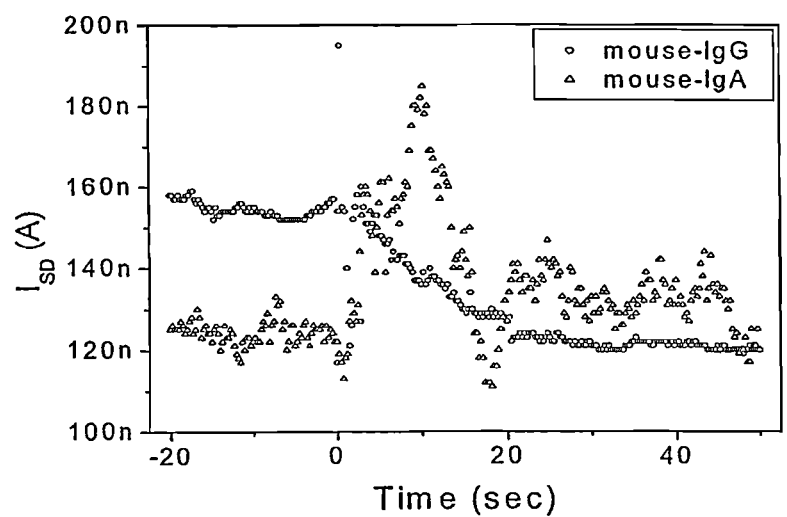

In certain embodiments, the response of a biotinylated n-type inversion-mode device to 1 nM streptavidin and avidin, introduced at time=0, is shown in FIG. 20A. These devices react with the opposite sense of the p-type accumulation-mode device shown in FIG. 15A. Additionally, two p-type nano-wire sensors are functionalized with goat-α-mouse IgG and demonstrate appropriately inverted and null responses to the presence of mouse IgG and mouse IgA, respectively. The mouse IgG and mouse IgA are at about 100 fM concentrations when introduced to the functionalized device at time t=0. The resulting conduction responses, as depicted in FIG. 20B, show opposite sense from the reaction of a p-type accumulation-mode device. Thus, the complementary sensing ability of the nano-wire sensors of the current invention has also been demonstrated for the detection of antibodies at less than about 100 fM concentration.

In certain implementations, measurements of current response may be taken at 0.25-second intervals with $V_{SD}$ and $V_{GD}$ held constant. For unfunctionalized sensor measurements, $V_{SD}$ may be set to −5V and $V_{GD}$ to −33V, while for functionalized sensor measurements, $V_{SD}$ may be set to −2V and $V_{GD}$ to −20V because research has shown that $V_{GD}$ of −20V is the optimal gate voltage. For implementations involving macromolecule addition, time=0 may be defined as the onset of protein/DNA addition. In addition, functionalization processes may run for about 100 seconds.

In certain exemplary configurations, a mixing device, such as the solution chamber of FIG. 6, is used to continuously mix solutions of interest after they are injected into a nano-sensor device. The volume of liquid in the solution chamber may be about 10 μL which includes 10 μL of buffer at the onset of each sensing run that is displaced by 100 μL of protein/DNA solution of which 10 μL remains.

The aforementioned nano-wire sensors have important medical diagnostic applications. For example, the sensors may be used to differentiate between healthy cells and diseased cells based on monitoring of real-time cellular responses. The efficiency of this technique lays in its label-free detection approach according to which cells being tests for pathogens do not need to be tagged with any visualization beacons or labels. In addition, the smoothness of the active surfaces of the nano-wire sensors and their large surface-to-volume ratio make these sensors highly sensitive to bound molecular charges, hence enabling accurate and efficient detection of specific label-free reagents. Moreover, the crystalline semiconductor materials used to fabricate these sensors facilitate their seamless integration into any CMOS systems, particular as a part of molecular or cellular arrays for performing wide-scaling complementary error detection and integrated signal processing.

The foregoing description of the preferred embodiment of the invention has been presented for the purposes of illustration and description. It is not intended to be exhaustive or to limit the invention to the precise form disclosed. Many modifications and variations are possible in light of the teaching herein.

We claim:

1. A sensor comprising:
a semiconductor layer formed in or on a substrate; and
a selectively functionalized channel having nano-scale cross-sectional dimensions etched from the semiconductor layer and forming an electrically conducting pathway between at least a first and second contact, said nano-scale channel having at least one exposed lateral face, wherein only the exposed lateral face or faces is functionalized.

2. The sensor of claim 1, wherein the semiconductor layer is formed of silicon and a lateral face has one of a (111) orientation, a (100) orientation, and a (110) orientation.

3. The sensor of claim 1, wherein said nano-scale channel has a trapezoidal, square, or rectangular cross-section.

4. The sensor of claim 3, wherein said lateral face is perpendicular to a base of the trapezoidal cross-section.

5. The sensor of claim 1, wherein said at least one lateral face is formed by anisotropic etching of the semiconductor layer.

6. The sensor of claim 1, wherein said at least one lateral face is formed by anisotropic wet etching.

7. The sensor of claim 1, wherein said at least one lateral face is smooth on an atomic scale.

8. The sensor of claim 1; wherein the substrate is a silicon wafer and an electrically insulating layer is disposed between the substrate and the semiconductor layer.

9. The sensor of claim 1, wherein said first and second contacts form a source and a drain contact, respectively, and a gate contact is applied on a top surface of the nano-scale channel distant to the substrate.

10. The sensor of claim 1, wherein the first and second contacts form a source and a drain contact, respectively, and one or more gate contacts are electrically connected to the substrate, wherein the one or more gate contacts are situated on at least one of a top surface, a bottom surface, and a lateral surface of the substrate.

11. The sensor of claim 8, wherein the first and second contacts form a source and a drain contact, respectively, and one or more gate contacts are electrically connected to the semiconductor layer, wherein the one or more gate contacts are perpendicular to a direction of current flow in the semiconductor layer.

12. The sensor of claim 1, wherein the semiconductor layer is p-type.

13. The sensor of claim 1, wherein the semiconductor layer is n-type.

14. The sensor of claim 3, wherein the nano-scale channel has a width at the top of the trapezoidal cross-section of less than about 10 nm.

15. The sensor of claim 1, wherein a thickness of an active region of the nano-scale channel is between about 25 nm to about 100 nm.

16. The sensor of claim 1, wherein a solution chamber is coupled to the sensor for mixing a plurality of fluids and supplying the mixed fluids to the sensor for liquid-phase electrical response characterization.

17. The sensor of claim 1, wherein a gate structure is coupled to the sensor for tuning sensitivity of the sensor to operate in a user-specifiable transconductance range.

18. The sensor of claim 1, wherein said nano-scale channel has a width selected to have the same order of magnitude as a Debye length (LD) of the semiconductor material from which the semiconductor layer is formed.

19. The sensor of claim 1, wherein the sensor is incorporated into an integrated CMOS system for performing at least one of signal processing, error detection, and complementary error detection.

20. The sensor of claim 19, wherein the integrated CMOS system includes at least one of an n-type inversion-mode sensor and a p-type accumulation-mode sensor.

21. The sensor of claim 1, wherein the first and second contacts form a source and a drain contact, respectively, and one or more gate contacts are electrically connected to the substrate, wherein the one or more gate contacts are situated on at least one of a top surface, a bottom surface, and a lateral surface of the substrate and wherein the nano-scale channel has a depletion width which depends on the semiconductor's Debye length (LD) of the semiconductor material from which the semiconductor layer is formed and the depletion width can be changed by applying a gate voltage to the one or more gate contacts.

* * * * *

SEQUENCE LISTING

<160> NUMBER OF SEQ ID NOS: 2

<210> SEQ ID NO 1
<211> LENGTH: 8
<212> TYPE: PRT
<213> ORGANISM: Mus musculus

<400> SEQUENCE: 1

Ser Ile Ile Asn Phe Glu Lys Leu
1               5

<210> SEQ ID NO 2
<211> LENGTH: 8
<212> TYPE: PRT
<213> ORGANISM: Mus musculus

<400> SEQUENCE: 2

Ser Ile Tyr Arg Tyr Tyr Gly Leu
1               5